US006833140B2

(12) United States Patent
Cundy et al.

(10) Patent No.: US 6,833,140 B2
(45) Date of Patent: Dec. 21, 2004

(54) ORALLY ADMINISTERED DOSAGE FORMS OF GABA ANALOG PRODRUGS HAVING REDUCED TOXICITY

(75) Inventors: Kenneth C. Cundy, Redwood City, CA (US); Mark A. Gallop, Los Altos, CA (US)

(73) Assignee: Xenoport, Inc., Santa Clara, CA (US)

( * ) Notice: Subject to any disclaimer, the term of this patent is extended or adjusted under 35 U.S.C. 154(b) by 251 days.

(21) Appl. No.: 10/170,127

(22) Filed: Jun. 11, 2002

(65) Prior Publication Data

US 2003/0083382 A1 May 1, 2003

Related U.S. Application Data

(60) Provisional application No. 60/297,521, filed on Jun. 11, 2001, provisional application No. 60/298,514, filed on Jun. 14, 2001, and provisional application No. 60/366,090, filed on Mar. 19, 2002.

(51) Int. Cl.[7] .............................. A61K 9/20; A61K 9/22; A61K 9/26; A01N 37/02; A01N 37/10
(52) U.S. Cl. ....................... 424/468; 424/464; 424/465; 424/468; 514/533; 514/547; 514/561
(58) Field of Search ................................ 424/464, 465, 424/468, 469; 514/533, 547, 561

(56) References Cited

U.S. PATENT DOCUMENTS

| 2,996,431 A | 8/1961 | Barry |
| 3,139,383 A | 6/1964 | Neville, Jr. |
| 3,402,240 A | 9/1968 | Cain et al. |
| 3,811,444 A | 5/1974 | Heller et al. |
| 3,845,770 A | 11/1974 | Theeuwes et al. |
| 3,916,899 A | 11/1975 | Theeuwes et al. |
| 3,962,414 A | 6/1976 | Michaels |
| 3,992,518 A | 11/1976 | Chien |
| 4,024,175 A | 5/1977 | Satzinger et al. |
| 4,036,829 A | 7/1977 | Ferres et al. |
| 4,063,064 A | 12/1977 | Saunders et al. |
| 4,066,747 A | 1/1978 | Capozza |
| 4,070,347 A | 1/1978 | Schmitt |
| 4,079,038 A | 3/1978 | Choi |
| 4,083,949 A | 4/1978 | Benedikt |
| 4,087,544 A | 5/1978 | Satzinger et al. |
| 4,088,864 A | 5/1978 | Theeuwes et al. |
| 4,093,709 A | 6/1978 | Choi et al. |
| 4,189,571 A | 2/1980 | Bodor et al. |
| 4,200,098 A | 4/1980 | Ayer et al. |
| 4,285,987 A | 8/1981 | Ayer et al. |
| 4,421,736 A | 12/1983 | Walters |
| 4,434,153 A | 2/1984 | Urquhart et al. |
| 4,611,056 A | 9/1986 | Guindon et al. |
| 4,721,613 A | 1/1988 | Urquhart et al. |
| 4,752,470 A | 6/1988 | Mehta |
| 4,760,057 A | 7/1988 | Alexander |
| 4,816,263 A | 3/1989 | Ayer et al. |
| 4,820,523 A | 4/1989 | Shtohryn et al. |
| 4,853,229 A | 8/1989 | Theeuwes |
| 4,916,230 A | 4/1990 | Alexander |
| 4,996,058 A | 2/1991 | Sinnreich et al. |
| 5,051,448 A | 9/1991 | Shashoua |
| 5,084,169 A | 1/1992 | Noble et al. |
| 5,091,184 A | 2/1992 | Khanna |
| 5,466,811 A | 11/1995 | Alexander |
| 5,563,175 A | 10/1996 | Silverman et al. |
| 5,672,584 A | 9/1997 | Borchardt et al. |
| 5,684,018 A | 11/1997 | Alexander |
| 5,698,155 A | 12/1997 | Grosswald et al. |
| 6,001,876 A | 12/1999 | Singh |
| 6,020,370 A | 2/2000 | Horwell et al. |
| 6,024,977 A | 2/2000 | Yatvin et al. |
| 6,028,214 A | 2/2000 | Silverman et al. |
| 6,103,932 A | 8/2000 | Horwell et al. |
| 6,117,906 A | 9/2000 | Silverman et al. |
| 6,127,418 A | 10/2000 | Bueno et al. |
| 6,171,615 B1 | 1/2001 | Roussin et al. |
| 6,375,987 B1 | 4/2002 | Farah et al. |
| 6,379,700 B2 | 4/2002 | Joachim et al. |
| 2002/0028806 A1 | 3/2002 | Goebel et al. |
| 2002/0055522 A1 | 5/2002 | Liebeschuetz et al. |
| 2002/0107208 A1 | 8/2002 | Chen et al. |
| 2003/0104053 A1 | 6/2003 | Gusler et al. |

FOREIGN PATENT DOCUMENTS

| EP | 0136893 A2 * | 4/1985 |
| EP | 0138481 B1 * | 4/1985 |
| EP | 0458751 A1 * | 11/1991 |
| EP | 1178034 A1 * | 2/2002 |
| EP | 1 178 034 A1 | 2/2002 |
| EP | 1201240 A2 * | 5/2002 |
| GB | 2362646 A1 * | 11/2001 |
| WO | WO 92/09560 A1 | 6/1992 |
| WO | WO 93/18070 A1 | 9/1993 |
| WO | WO 93/23383 A1 | 11/1993 |
| WO | WO 93/25197 A1 | 12/1993 |
| WO | WO 95/10519 A1 | 4/1995 |
| WO | WO 96/38435 A1 | 12/1996 |
| WO | WO 97/29101 A1 | 8/1997 |
| WO | WO 97/33858 A1 | 9/1997 |
| WO | WO 97/33859 A1 | 9/1997 |
| WO | WO 98/04537 A1 | 2/1998 |

(List continued on next page.)

OTHER PUBLICATIONS

U.S. Appl. No. 10/171,485, Gallop et al.
U.S. Appl. No. 10/167,797, Gallop et al.

(List continued on next page.)

Primary Examiner—James M. Spear
Assistant Examiner—S. Tran
(74) Attorney, Agent, or Firm—Sunil K. Singh; Cooley Godward LLP

(57) ABSTRACT

The present invention provides an extended release oral dosage form of prodrugs of gabapentin and other GABA analogs, which dosage forms exhibit reduced toxicity. The dosage forms are particularly useful in administering those prodrugs of gabapentin and other GABA analogs that are metabolized to form an aldehyde. The dosage forms of the invention are useful for treating or preventing diseases and/or disorders for which the parent gabapentin or other GABA analog are known to be therapeutically effective.

29 Claims, No Drawings

FOREIGN PATENT DOCUMENTS

| WO | WO 98/06402 A1 | 2/1998 |
|---|---|---|
| WO | WO 98/17627 A1 | 4/1998 |
| WO | WO 99/00127 A1 | 1/1999 |
| WO | WO 99/08671 A1 | 2/1999 |
| WO | WO 99/21824 A1 | 5/1999 |
| WO | WO 99/31057 A1 | 6/1999 |
| WO | WO 99/31074 A2 | 6/1999 |
| WO | WO 99/31075 A1 | 6/1999 |
| WO | WO 99/37296 A1 | 7/1999 |
| WO | WO 99/61424 A1 | 12/1999 |
| WO | WO 00/15611 A1 | 3/2000 |
| WO | WO 00/23067 A1 * | 4/2000 |
| WO | WO 00/31020 A1 * | 6/2000 |
| WO | WO 00/50027 A1 * | 8/2000 |
| WO | WO 00/73298 A1 * | 12/2000 |
| WO | WO 01/42191 A1 * | 6/2001 |
| WO | WO 01/54481 A2 * | 8/2001 |
| WO | WO 01/62242 A1 * | 8/2001 |
| WO | WO 01/90052 A1 * | 11/2001 |
| WO | WO 01/90081 A1 * | 11/2001 |
| WO | WO 02/00209 A2 * | 1/2002 |
| WO | WO 02/04458 A1 * | 1/2002 |
| WO | WO 02/04459 A1 * | 1/2002 |
| WO | WO 02/10120 A1 * | 2/2002 |
| WO | WO 02/18327 A2 * | 3/2002 |
| WO | WO 02/28411 A1 * | 4/2002 |
| WO | WO 02/28881 A1 * | 4/2002 |
| WO | WO 02/28883 A1 * | 4/2002 |
| WO | WO 02/32376 A2 * | 4/2002 |
| WO | WO 02/34711 A1 * | 5/2002 |
| WO | WO 02/42414 A2 * | 5/2002 |
| WO | WO 02/062766 A1 * | 8/2002 |
| WO | WO 02/096404 A1 * | 12/2002 |
| WO | WO 02/100347 A2 * | 12/2002 |
| WO | WO 02/100392 A1 * | 12/2002 |
| WO | WO 03/000250 A1 * | 1/2003 |
| WO | WO 03/005971 A2 * | 1/2003 |
| WO | WO 03/011255 A1 * | 2/2003 |
| WO | WO 03/035040 A1 * | 5/2003 |

OTHER PUBLICATIONS

Alderman, "A Review of Cellulose Ethers in Hydrophilic Matrices for Oral Controlled–Release Dosage Forms," *Int. J. Pharm. Tech. & Prod. Mfr.* (1984) 5(3):1–9.

Bamba et al., "Release Mechanisms in Gelforming Sustained Release Preparations" *Int. J. Pharm.* (1979) 2:307.

Butcher Carbamate Esters: a Simple, Mild Method of Formation. *SynLett* (1994) 825–826.

Coleman et al., *Polymers* (1990) 31, 1187–1231.

During et al., "Controlled Release of Dopamine From a Polymeric Brain Implant; In Vivo Characterization," *Ann. Neurol.* (1989) 25:351.

Fincher, *J. Pharm. Sci.* (1968) 57, 1825–1835.

Goodson, in "Medical Applications of Controlled Release," vol. 2, pp. 115–138 (1984) Langer and Wise (eds) CRC Press, Boca Raton, FLA.

Howard et al., *J. Neurosurg.* (1989) 71:105.

Kayser et al., "Designer Yeast: an Enantioselective Oxidizing Reagent for Organic Synthesis." *SynLett* (1999) 1:153.

Langer, "New Methods of Drug Delivery," *Science* (1990) 249: 1527–1533.

Langer, "Chemical and Physical Structure of Polymers as Carriers for Controlled Release of Bioactive Agents: A Review," *JMS—Macromol. Chem Phys* (1983), C23(1): 61–126.

Leong et al., "Polymeric Controlled Drug Delivery" *Adv. Drug Delivery Rev.* (1987) 1:199–233.

Levy et al., "Inhibition of Calcification of Bioprosthetic Heart Valves by Local Controlled Release Diphosphonate," *Science* (1985) 228: 190–2.

Lu, "Dimensionless Presentation for Drug Release From A Coated Pure Drug Bead: 2. Experiment," *Int. J. Pharm.* (1994) 112, 117–124.

Renz et al., "100 years of Baeyer–Villiger Oxidations," *Eur. J. Org. Chem.* (1999) 737–750.

Roerdink et al., *Drug Carrier Systems* (1989)9, 57–110.

Rosoff, *Controlled Release of Drugs* Chap. 2, (1989) pp. 53–95.

Saudek et al, "A Preliminary Trial of the Programmable Implantable Medication System for Insulin Delivery," *N. Engl. J. Med.* (1989) 321:574–579.

Sefton "Implantable Pumps," *CRC Crit. Rev. Biomed. Eng.* (1987) 14(3): 201–240.

Stevenson et al., "Colonic Absorption of Antiepileptic Agents," (1997) *Epilepsia* 38(1): 63–7.

Stewart, "Cyclohexanone Monooxygenase: A Useful Reagent For Asymmetric Baeyer–Villiger Reactions," *Current Organic Chemistry* (1998) 2:195–216.

Strukul, "Transition Metal Catalysis in the Baeyer–Villiger Oxidation of Ketones," *Angnew. Chem. Int. Ed.* (1998) 37:1198–1209.

Verma et al., "Osmotically Controlled Oral Drug Delivery," *Drug Develop. Indus. Pharm.* (2000), 26(7): 695–708.

Alexander, et al. "Investigation of (Oxodioxolenyl)menthyl Carbamates as Nonchiral Bioreversible Prodrug Moieties for Chiral Amines," *Med Chem.* (1996) 39, 480–486.

Sun, et al. "A General Synthesis of Dioxolenone Prodrug moieties," *Tetrahedron Letters* (2002) 1161–1164.

* cited by examiner

ORALLY ADMINISTERED DOSAGE FORMS OF GABA ANALOG PRODRUGS HAVING REDUCED TOXICITY

This application claims the benefit under 35 U.S.C. § 119(e) from U.S. Provisional Application Ser. No. 60/297,521 filed Jun. 11, 2001; U.S. Provisional Application Ser. No. 60/298,514 filed Jun. 14, 2001; and U.S. Provisional Application Ser. No. 60/366,090 filed Mar. 19, 2002, which are herein incorporated by reference.

FIELD OF THE INVENTION

The present invention relates generally to prodrugs of GABA analogs which are adapted to be administered orally, and dosage forms for administering these prodrugs of GABA analogs to reduce their toxicity.

BACKGROUND OF THE INVENTION

Gamma ("γ")-aminobutyric acid ("GABA") is one of the major inhibitory transmitters in the central nervous system of mammals. GABA is not transported efficiently into the brain from the bloodstream (i.e., GABA does not effectively cross the blood-brain barrier). Consequently, brain cells provide virtually all of the GABA found in the brain (GABA is biosynthesized by decarboxylation of glutamic acid with pyridoxal phosphate).

GABA regulates neuronal excitability through binding to specific membrane proteins (i.e., GABAA receptors), which results in opening of an ion channel. The entry of chloride ion through the ion channel leads to hyperpolarization of the recipient cell, which consequently prevents transmission of nerve impulses to other cells. Low levels of GABA have been observed in individuals suffering from epileptic seizures, motion disorders (e.g., multiple sclerosis, action tremors, tardive dyskinesia), panic, anxiety, depression, alcoholism and manic behavior.

The implication of low GABA levels in a number of common disease states and/or common medical disorders has stimulated intensive interest in preparing GABA analogs, which have superior pharmaceutical properties in comparison to GABA (e.g., the ability to cross the blood brain barrier). Accordingly, a number of GABA analogs, with considerable pharmaceutical activity have been synthesized in the art (See, e.g., Satzinger et al., U.S. Pat. No. 4,024,175; Silverman et al., U.S. Pat. No. 5,563,175; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Publication No. WO 92/09560; Silverman et al., International Publication No. WO 93/23383; Horwell et al., International Publication No. WO 97/29101, Horwell et al., International Publication No. WO 97/33858; Horwell et al., International Publication No. WO 97/33859; Bryans et al., International Publication No. WO 98/17627; Guglietta et al., International Publication No. WO 99/08671; Bryans et al., International Publication No. WO 99/21824; Bryans et al., International Publication No. WO 99/31057; Belliotti et al., International Publication No. WO 99/31074; Bryans et al., International Publication No. WO 99/31075; Bryans et al., International Publication No. WO 99/61424; Bryans et al., International Publication No. WO 00/15611; Bryans, International Publication No. WO 00/31020; Bryans et al., International Publication No. WO 00/50027; and Bryans et al., International Publication No. WO 02/00209).

However, many GABA analogs, including those described above exhibit poor oral absorption across the gut wall. One potential solution to the above problem is converting GABA analogs to prodrugs of GABA analogs (Bryans et al., International Publication No. WO 01/90052; U.K. Application GB 2,362,646; European Applications EP 1,201,240 and 1,178,034; Yatvin et al., U.S. Pat. No. 6,024,977; Gallop et al., U.S. patent application Ser. No. 10/171,485, entitled "Prodrugs of GABA Analogs, Compositions and Uses Thereof"; Gallop et al International Publication No. WO 02/28881; Gallop et al, International Publication No. WO 02/28883; Gallop et al, International Publication No. WO 02/28411; Gallop et al, International Publication No. WO 02/32376; Gallop et al, International Publication No. WO 02/42414). Typically, in a prodrug, a polar functional group (e.g., a carboxylic acid, an amino group, a hydroxyl group, etc.) is masked by a promoiety, which is labile under physiological conditions. Accordingly, prodrugs are usually transported through hydrophobic biological barriers such as membranes and typically possess superior physicochemical properties in comparison to the parent drug.

Pharmacologically effective prodrugs are ideally non-toxic and are preferably selectively cleaved at the locus of drug action. Ideally, cleavage of the promoiety occurs rapidly and quantitatively with the formation of non-toxic by-products (i.e., the hydrolyzed promoiety).

Many GABA analog prodrugs exhibit unacceptable toxicity when administered orally in conventional dosage forms. In part this is due to the high doses required for many GABA analog therapy and in part because most of the therapeutic indications for GABA analogs require long-term chronic administration (i.e., administration for periods of months, years or even for the remaining lifetime of the patient). Additional problems may be caused by the chemical structure of the promoiety, which may hydrolyze to toxic metabolites (e.g., aldehydes or acids).

Accordingly, what is needed is a method for reducing toxicity when administering prodrugs of GABA analogs. Ideally, the above method is particularly effective when the promoiety hydrolyzes to provide toxic metabolites.

SUMMARY OF THE INVENTION

The present invention addresses these and other needs by providing oral dosage forms for prodrugs of GABA analogs which exhibits lower toxicity than conventional oral dosage forms of these same prodrugs. The oral dosage form of the present invention has particular utility in administering prodrugs of GABA analogs which are metabolized to form an aldehyde. In addition, the dosage forms of the present invention may be used to administer prodrugs of GABA analogs which are metabolized to form acids which deplete the body's carnitine reserves. The present invention also provides methods for treating patients using these dosage forms.

In one aspect, the current invention comprises an oral sustained release dosage form for administering a prodrug of a GABA analog. In another aspect, the invention comprises a method of reducing toxicity of orally administered GABA analogs. The above method includes formulating the GABA analog as a prodrug, comprised of the GABA analog covalently bound to a cleavable promoiety. The GABA analog prodrug is placed in a sustained release oral dosage form and the dosage form is introduced into an intestinal lumen of a patient by having the patient swallow the dosage form. The method further includes releasing the prodrug gradually from the swallowed dosage form into the intestinal lumen of the patient over a period of hours and allowing the GABA analog to be cleaved from the promoiety after swallowing to provide a therapeutic concentration of the GABA analog in the blood plasma of the patient. When following this method, the toxicity of the prodrug of the GABA analog is less than a toxicity of an equivalent dose of the prodrug administered from an immediate release oral dosage form. In one preferred embodiment, the prodrug is metabolized to form an aldehyde (e.g., formaldehyde). In another embodiment, the prodrug is metabolized to form an acid which depletes the body's carnitine reserves, (e.g., pivalic acid).

Preferably, the prodrug is released from the dosage form over a period of at least about 6 hours, more preferably, over a period of at least about 8 hours, and most preferably, over a period of at least about 12 hours. Further, the dosage form preferably releases from 0 to 20% of the prodrug in 0 to 2 hours, from 20 to 50% of the prodrug in 2 to 12 hours, from 50 to 85% of the prodrug in 3 to 20 hours and greater than 75% of the prodrug in 5 to 18 hours.

In a preferred embodiment, the current invention provides an oral dosage form of a prodrug of a GABA analog, wherein the dosage form, upon swallowing, provides a curve of concentration of the GABA analog in the plasma over time, the curve having an area under the curve (AUC) which is proportional to the dose of GABA analog administered, and preferably, also has a maximum concentration $C_{max}$ that is proportional to the dose of GABA analog administered. In one embodiment, the $C_{max}$ is less than 75%, and is preferably less than 60%, of the $C_{max}$ obtained from administering an equivalent dose of the prodrug from an immediate release oral dosage form. Preferably, the AUC is at least 50% of the AUC obtained from administering an equivalent dose of the prodrug from an immediate release oral dosage form((more preferably, at least 75% of the AUC obtained from administering an equivalent dose of the prodrug from an immediate release oral dosage form) and most preferably, substantially the same as, the AUC obtained from administering an equivalent dose of the prodrug from an immediate release oral dosage form).

The oral sustained release dosage forms of the present invention can take any form as long as the release characteristics and pharmacokinetic profiles above are satisfied. For example, the dosage form can be in the form of an osmotic dosage form, a prodrug-releasing polymer, prodrug-releasing tiny timed-release pills, prodrug-releasing lipids, prodrug-releasing waxes and/or prodrug releasing beads.

The dosage forms and administration methods of the present invention may be useful for treating or preventing epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders or ethanol withdrawal syndrome.

DISCLOSURE OF THE INVENTION

Definitions

"Active transport or active transport process" refers to the movement of molecules across cellular membranes that:
  a) is directly or indirectly dependent on an energy mediated process (i.e., driven by ATP hydrolysis, ion gradient, etc.); or
  b) occurs by facilitated diffusion mediated by interaction with specific transporter proteins.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 20 carbon atoms, more preferably, from 1 to 10 carbon atoms.

"Alkanyl" refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, cylcohexylcarbonyl, cyclohexylmethylcarbonyl, benzoyl, benzylcarbonyl and the like.

"Acylamino" (or alternatively "acylamido") refers to a radical —NR'C(O)R, where R' and R are each independently hydrogen, alkyl, cycloalkyl, cycloheteroalkyl, aryl, arylalkyl, heteroalkyl, heteroaryl, heteroarylalkyl, as defined herein. Representative examples include, but are not limited to, formylamino, acetylamino (i.e., acetamido), cyclohexylcarbonylamino, cyclohexylmethylcarbonylamino, benzoylamino (i.e., benzamido), benzylcarbonylamino and the like.

"Acyloxy" refers to a radical —OC(O)R, where R is hydrogen, alkyl, cycloalkyl, cycloheteroalkyl, aryl, arylalkyl, heteroalkyl, heteroaryl or heteroarylalkyl, as defined herein. Representative examples include, but are not limited to, acetyloxy (or acetoxy), butyloxy (or butoxy), benzoyloxy and the like.

"Alkylamino" means a radical —NHR where R represents an alkyl or cycloalkyl group as defined herein. Representative examples include, but are not limited to, methylamino, ethylamino, 1-methylethylamino, cyclohexyl amino and the like.

"Alkoxy" refers to a radical —OR where R represents an alkyl or cycloalkyl group as defined herein. Representative examples include, but are not limited to, methoxy, ethoxy, propoxy, butoxy, cyclohexyloxy and the like.

"Alkoxycarbonyl" refers to a radical —C(O)-alkoxy where alkoxy is as defined herein.

"Alkylsulfonyl" refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR where R is an alkyl or cycloalkyl group as defined herein that may be optionally substituted as defined herein. Representative examples include, but are not limited to methylthio, ethylthio, propylthio, butylthio and the like.

"Amino" refers to the radical —NH$_2$.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably between 6 to 12 carbon atoms.

"Arylalkyl" refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is (C$_6$–C$_{30}$) arylalkyl, e.g., the alkanyl, alkenyl or alkynyl moiety of the arylalkyl group is (C$_1$–C$_{10}$) and the aryl moiety is (C$_6$–C$_{20}$), more preferably, an arylalkyl group is (C$_6$–C$_{20}$) arylalkyl, e.g., the alkanyl, alkenyl or alkynyl moiety of the arylalkyl group is (C$_1$–C$_8$) and the aryl moiety is (C$_6$–C$_{12}$).

"Arylalkyloxy" refers to an —O-arylalkyl group where arylalkyl is as defined herein.

"Aryloxycarbonyl" refers to a radical —C(O)—O-aryl where aryl is as defined herein.

"AUC" is the area under the plasma drug concentration-versus-time curve extrapolated from zero time to infinity.

"Bridged cycloalkyl" refers to a radical selected from the group consisting of

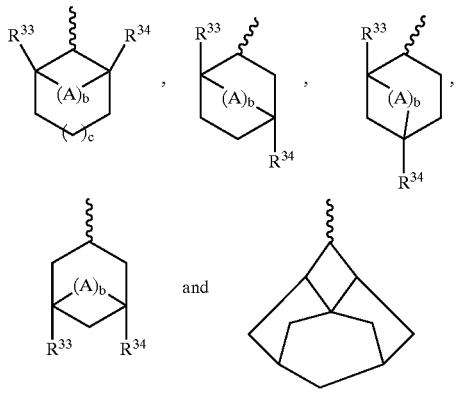

wherein:

A is $(CR^{35}R^{36})_b$;

$R^{35}$ and $R^{36}$ are independently selected from the group consisting of hydrogen and methyl;

$R^{33}$ and $R^{34}$ are independently selected from the group consisting of hydrogen and methyl;

b is an integer from 1 to 4; and c is an integer from 0 to 2.

"Carbamoyl" refers to the radical —C(O)N(R)$_2$ where each R group is independently hydrogen, alkyl, cycloalkyl or aryl as defined herein, which may be optionally substituted, as defined herein.

"Carboxy" means the radical —C(O)OH.

"Carcinogenic potency (TD$_{50}$)" (see Peto et al., *Environmental Health Perspectives* 1984, 58, 1–8) is defined for a particular compound in a given animal species as that chronic dose-rate in mg/kg body wt/day which would induce tumors in half the test animals at the end of a standard lifespan for the species. Since the tumor(s) of interest often does occur in control animals, TD$_{50}$ is more precisely defined as: that dose-rate in mg/kg body wt/day which, if administered chronically for the standard lifespan of the species, will halve the probability of remaining tumorless throughout that period. A TD$_{50}$ can be computed for any particular type of neoplasm, for any particular tissue, or for any combination of these.

"C$_{max}$" is the highest drug concentration observed in plasma following an extravascular dose of drug.

"Compounds used in the invention" refers to GABA analog prodrug compounds encompassed by generic formulae disclosed herein and includes any specific compounds within that formula whose structure is disclosed herein. The compounds used in the invention may be identified either by their chemical structure and/or chemical name. When the chemical structure and chemical name conflict, the chemical structure is determinative of the identity of the compound. The compounds used in the invention may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds used in the invention may also exist in several tautomeric forms including the enol form, the keto form and mixtures thereof. Accordingly, the chemical structures depicted herein encompass all possible tautomeric forms of the illustrated compounds. The compounds used in the invention also include isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$. Further, it should be understood, when partial structures of the compounds used in the invention are illustrated, that brackets indicate the point of attachment of the partial structure to the rest of the molecule.

"Composition used in the invention" refers to at least one GABA analog prodrug used in the invention and a pharmaceutically acceptable vehicle, with which the prodrug is administered to a patient. When administered to a patient, the prodrugs are administered in isolated form, which means separated from a synthetic organic reaction mixture.

"Cyano" means the radical —CN.

"Cycloalkyl" refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. Preferably, the cycloalkyl group is $(C_3-C_{10})$ cycloalkyl, more preferably $(C_3-C_7)$ cycloalkyl.

"Cycloheteroalkyl" refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Cycloheteroalkyloxycarbonyl" refers to a radical —C(O)—OR where R is cycloheteroalkyl is as defined herein.

"Derived from a bile acid" refers to a moiety that is structurally related to a compound of Formulae (V) or (VI):

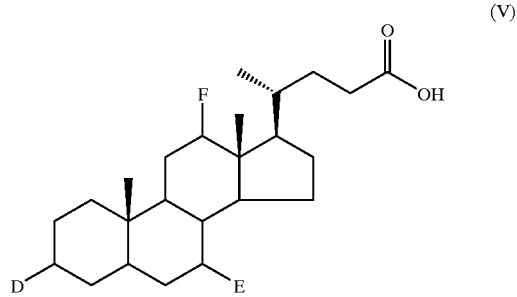

(V)

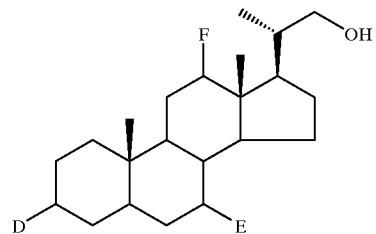

(VI)

wherein each of D, E and F are independently H or OH.

The structure of the moiety is identical to the compound except at 1 or 2 positions. At these positions, a hydrogen atom attached to a hydroxyl group and/or the hydroxyl moiety of the carboxylic acid group has been replaced with a covalent bond that serves as a point of attachment to another moiety, which is preferably a GABA analog.

"Derived from a GABA analog" refers to a moiety that is structurally related to a GABA analog. The structure of the moiety is identical to the compound except at 1 or 2 positions. At these positions, a hydrogen atom attached to the amino group and (optionally) the hydroxyl moiety of the carboxylic acid group has been replaced with a covalent bond that serves as a point of attachment to another moiety.

"Dialkylamino" means a radical —NRR' where R and R' independently represent an alkyl or cycloalkyl group as defined herein. Representative examples include, but are not limited to, dimethylamino, methylethylamino, di-(1-methylethyl)amino, (cyclohexyl)(methyl)amino, (cyclohexyl)(ethyl)amino, (cyclohexyl)(propyl)amino and the like.

"GABA analog" refers to a compound, unless specified otherwise, as having the following structure:

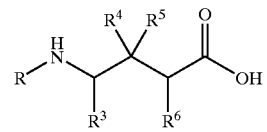

wherein:
R is hydrogen, or R and $R^6$ together with the atoms to which they are attached form an azetidine, substituted azetidine, pyrrolidine or substituted pyrrolidine ring;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl; and $R^4$ and $R^5$ are independently selected from the group consisting of hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl or optionally, $R^4$ and $R^5$ together with the carbon atom to which they are attached form a cycloalkyl, substituted cycloalkyl, cycloheteroalkyl, substituted cycloheteroalkyl or bridged cycloalkyl ring.

"Halo" means fluoro, chloro, bromo, or iodo.

"Heteroalkyloxy" means an —O-heteroalkyl group where heteroalkyl is as defined herein.

"Heteroalkyl, Heteroalkanyl, Heteroalkenyl, Heteroalkynyl" refer to alkyl, alkanyl, alkenyl and alkynyl radical, respectively, in which one or more of the carbon atoms (and any associated hydrogen atoms) are each independently replaced with the same or different heteroatomic groups. Typical heteroatomic groups include, but are not limited to, —O—, —S—, —O—O—, —S—S—, —O—S—, —NR'—, =N—N=, —N=N—, —N=N—NR'—, —PH—, —P(O)$_2$—, —O—P(O)$_2$—, —S(O)—, —S(O)$_2$—, —SnH$_2$— and the like, where R' is hydrogen, alkyl, substituted alkyl, cycloalkyl, substituted cycloalkyl, aryl or substituted aryl.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5–20 membered heteroaryl, more preferably between 5–10 membered heteroaryl. Preferred heteroaryl groups are those derived from thiophene, pyrrole, benzothiophene, benzofuran, indole, pyridine, quinoline, imidazole, oxazole and pyrazine.

"Heteroaryloxycarbonyl" refers to a radical —C(O)—OR where R is heteroaryl as defined herein.

"Heteroarylalkyl" refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In preferred embodiments, the heteroarylalkyl group is a 6–30 membered heteroarylalkyl, e.g., the alkanyl, alkenyl or alkynyl moiety of the heteroarylalkyl is 1–10 membered and the heteroaryl moiety is a 5–20-membered heteroaryl, more preferably, 6–20 membered heteroarylalkyl, e.g., the alkanyl, alkenyl or alkynyl moiety of the heteroarylalkyl is 1–8 membered and the heteroaryl moiety is a 5–12-membered heteroaryl.

"Passive diffusion" refers to uptake of an agent that is not mediated by a specific transporter protein. An agent that is substantially incapable of passive diffusion has a permeabilty across a standard cell monolayer (e.g., Caco-2) in vitro of less than 5×10$^{-6}$ cm/sec, and usually less than 1×10$^{-6}$ cm/sec (in the absence of an efflux mechanism).

"Patient" includes humans. The terms "human" and "patient" are used interchangeably herein.

"Pharmaceutically acceptable" means approved or approvable by a regulatory agency of the Federal or a state government or listed in the U.S. Pharmacopoeia or other generally recognized pharmacopeias for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently (though not necessarily) pharmacologically inactive until converted to the parent drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1–8 (John Wiley and Sons, 1971–1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are each independently replaced with the same or different substituent(s). Typical substituents include, but are not limited to, —X, —R$^{29}$, —O$^-$, =O, —OR$^{29}$, —SR$^{29}$, —S$^-$, =S, —NR$^{29}$R$^{30}$, =NR$^{29}$, —CX$_3$, —CF$_3$, —CN, —OCN, —SCN, —NO, —NO$_2$, =N$_2$, —N$_3$, —S(O)$_2$O$^{31}$, —S(O)$_2$OH, —S(O)$_2$R$^{29}$, —OS(O$_2$)O$^-$, —OS(O)$_2$R$^{29}$, —P(O)(O$^-$)$_2$, —P(O)(OR$^{29}$)(O$^-$), —OP(O)(OR$^{29}$)(OR$^{30}$), —C(O)R$^{29}$, —C(S)R$^{29}$, —C(O)OR$^{29}$, —C(O)NR$^{29}$R$^{30}$, —C(O)O$^-$, —C(S)OR$^{29}$, —NR$^{31}$C(O)NR$^{29}$R$^{30}$, —NR$^{31}$C(S)NR$^{29}$R$^{30}$, —NR$^{31}$C(NR$^{29}$)NR$^{29}$R$^{30}$ and —C(NR$^{29}$)NR$^{29}$R$^{30}$, where each X is independently a halogen; each R$^{29}$ and R$^{30}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{31}$R$^{32}$, —C(O)R$^{31}$ or —S(O)$_2$R$^{31}$ or optionally R$^{29}$ and R$^{30}$ together with the atom to which they are both attached form a cycloheteroalkyl or substituted cycloheteroalkyl ring; and R$^{31}$ and R$^{32}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Transporter protein" refers to a protein that has a direct or indirect role in transporting a molecule into and/or through a cell. For example, a transporter protein may be, but is not limited to, solute carrier transporters, co-transporters, counter transporters, uniporters, symporters, antiporters, pumps, equilibrative transporters, concentrative transporters and other proteins, which mediate active transport, energy-dependent transport, facilitated diffusion, exchange mechanisms and specific absorption mechanisms. Transporter proteins, may also be, but are not limited to, membrane-bound proteins that recognize a substrate and effect its entry into or exit from a cell by a carrier-mediated transporter or by receptor-mediated transport. A transporter protein, may also be, but is not limited to, an intracellularly expressed protein that participates in trafficking of substrates through or out of a cell. Transporter proteins, may also be, but are not limited to, proteins or glycoproteins exposed on the surface of a cell that do not directly transport a substrate but bind to the substrate holding it in proximity to a receptor or transporter protein that effects entry of the substrate into or through the cell. Examples of carrier proteins include: the intestinal and liver bile acid transporters, dipeptide transporters, oligopeptide transporters, simple sugar transporters (e.g., SGLT1), phosphate transporters, monocarboxcylic acid transporters, P-glycoprotein transporters, organic anion transporters (OAT), and organic cation transporters. Examples of receptor-mediated transport proteins include: viral receptors, immunoglobulin receptors, bacterial toxin receptors, plant lectin receptors, bacterial adhesion receptors, vitamin transporters and cytokine growth factor receptors.

"Toxic" and "toxicity" refers to a medically measurable undesirable effect in a patient to which a particular drug has been orally administered. In the case of a prodrug with an aldehyde-producing promoiety, the terms "toxic" and "toxicity" refer to effects such as carcinogenicity, irritation, mucosal damage, gastritis, hyperkeratosis, elevation of liver enzymes (e.g., transaminases) and fertility impairment. In the case of a prodrug that releases gabapentin or other GABA analogs upon cleavage, the terms "toxic" and "toxicity" mean an undesirable side-effects, such as somnolence, dizziness, ataxia, choreoathetosis, nystagmus or dyspepsia, caused by an undesirably high concentration of the parent compound in the systemic circulation of the patient.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

Sustained Release Oral Dosage Forms of the Invention

The present invention can be practiced with a number of different dosage forms, which may be adapted to provide sustained release of the prodrug upon oral administration.

In one embodiment of the invention, the dosage form comprises beads that on dissolution or diffusion release the prodrug over an extended period of hours, preferably, over a period of at least 6 hours, more preferably, over a period of at least 8 hours and most preferably, over a period of at least 12 hours. The prodrug-releasing beads may have a central composition or core comprising a prodrug and pharmaceutically acceptable vehicles, including an optional lubricant, antioxidant and buffer. The beads may be medical preparations with a diameter of about 1 to 2 mm. Individual beads may comprise doses of the prodrug, for example, doses of up to about 40 mg of prodrug. The beads, in one embodiment, are formed of non-cross-linked materials to enhance their discharge from the gastrointestinal tract. The beads may be coated with a release rate-controlling polymer that gives a timed release profile.

The time release beads may be manufactured into a tablet for therapeutically effective prodrug administration. The beads can be made into matrix tablets by the direct compression of a plurality of beads coated with, for example, an acrylic resin and blended with excipients such as hydroxypropylmethyl cellulose. The manufacture of beads has been disclosed in the art (Lu, *Int. J. Pharm.*, 1994, 112, 117–124; Pharmaceutical Sciences by Remington, 14$^{th}$ ed, pp1626–1628 (1970); Fincher, *J. Pharm. Sci.* 1968, 57, 1825–1835 ( ); and U.S. Pat. No. 4,083,949) as has the manufacture of tablets (Pharmaceutical Sciences, by Remington, 17$^{th}$ Ed, Ch. 90, pp1603–1625 (1985).

In another embodiment, an oral sustained release pump may be used (see Langer, supra; Sefton, 1987, *CRC Crit Ref Biomed Eng.* 14:201; Saudek et al., 1989, *N. Engl. J Med.* 321:574).

In another embodiment, polymeric materials can be used (see "Medical Applications of Controlled Release," Langer and Wise (eds.), CRC Press., Boca Raton, Fla. (1974); "Controlled Drug Bioavailability," Drug Product Design and Performance, Smolen and Ball (eds.), Wiley, N.Y. (1984); Ranger and Peppas, 1983, *J Macromol. Sci. Rev. Macromol Chem.* 23:61; see also Levy et al., 1985, *Science* 228: 190; During et al., 1989, *Ann. Neurol.* 25:351; Howard et al, 1989, *J. Neurosurg.* 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described (Alderman, *Int. J. Pharm. Tech. & Prod. Mfr.*, 1984, 5(3) 1–9). Factors affecting drug release are well known to the skilled artisan and have been described in the art (Bamba et al., *Int. J. Pharm.*, 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In yet another embodiment, drug-releasing lipid matrices can be used for oral sustained release administration. One particularly preferred example is when solid microparticles of the prodrug are coated with a thin controlled release layer of a lipid (e.g., glyceryl behenate and/or glyceryl palmitostearate) as disclosed in Farah et al., U.S. Pat. No. 6,375,987 and Joachim et al., U.S. Pat. No. 6,379,700. The lipid-coated particles can optionally be compressed to form a tablet. Another controlled release lipid-based matrix material which is suitable for sustained release oral administration comprises polyglycolized glycerides as disclosed in Roussin et al., U.S. Pat. No. 6,171,615.

In yet another embodiment, prodrug-releasing waxes can be used for oral sustained release administration. Examples of suitable sustained prodrug-releasing waxes are disclosed in Cain et al., U.S. Pat. No. 3,402,240 (carnauba wax, candedilla wax, esparto wax and ouricury wax); Shtohryn et al. U.S. Pat. No. 4,820,523 (hydrogenated vegetable oil, bees wax, caranuba wax, paraffin, candelillia, ozokerite and mixtures thereof); and Walters, U.S. Pat. No. 4,421,736 (mixture of paraffin and castor wax).

In still another embodiment, osmotic delivery systems are used for oral sustained release administration (Verma et al., *Drug Dev. Ind. Pharm.*, 2000, 26:695–708). In a preferred embodiment, OROS® systems made by Alza Corporation, Mountain View, Calif. are used for oral sustained release delivery devices (Theeuwes et al., U.S. Pat. No. 3,845,770; Theeuwes et al., U.S. Pat. No. 3,916,899).

In yet another embodiment, a controlled-release system can be placed in proximity of the target of the prodrug of the GABA analog, thus requiring only a fraction of the systemic dose (see, e.g., Goodson, in "Medical Applications of Controlled Release," supra, vol. 2, pp. 115–138 (1984)). Other controlled-release systems discussed in Langer, 1990, *Science* 249:1527–1533 may also be used.

In another embodiment of the invention, the dosage form comprises a prodrug of a GABA analog coated on a polymer substrate. The polymer can be an erodible, or a nonerodible polymer. The coated substrate may be folded onto itself to provide a bilayer polymer drug dosage form. For example prodrug of a GABA analog can be coated onto a polymer such as a polypeptide, collagen, gelatin, polyvinyl alcohol, polyorthoester, polyacetyl, or a polyorthocarbonate and the coated polymer folded onto itself to provide a bilaminated dosage form. In operation, the bioerodible dosage form erodes at a controlled rate to dispense the prodrug over a sustained release period. Representative biodegradable polymer comprise a member selected from the group consisting of biodegradable poly(amides), poly (amino acids), poly(esters), poly(lactic acid), poly(glycolic acid), poly (carbohydrate), poly(orthoester), poly (orthocarbonate), poly(acetyl), poly(anhydrides), biodegradable poly (dehydropyrans), and poly(dioxinones) which are known in the art (Rosoff, *Controlled Release of Drugs*, Chap. 2, pp. 53–95 (1989); and in U.S. Pat. Nos. 3,811,444; 3,962,414; 4,066,747, 4,070,347; 4,079,038; and 4,093,709).

In another embodiment of the invention, the dosage form comprises a prodrug loaded into a polymer that releases the prodrug by diffusion through a polymer, or by flux through pores or by rupture of a polymer matrix. The drug delivery polymeric dosage form comprises a concentration of 10 mg to 2500 mg homogenously contained in or on a polymer. The dosage form comprises at least one exposed surface at the beginning of dose delivery. The non-exposed surface, when present, is coated with a pharmaceutically acceptable material impermeable to the passage of a prodrug. The dosage form may be manufactured by procedures known in the art. An example of providing a dosage form comprises blending a pharmaceutically acceptable carrier like polyethylene glycol, with a known dose of prodrug at an elevated temperature, like 37° C., and adding it to a silastic medical grade elastomer with a cross-linking agent, for example, octanoate, followed by casting in a mold. The step is repeated for each optional successive layer. The system is allowed to set for 1 hour, to provide the dosage form. Representative polymers for manufacturing the dosage form comprise a member selected from the group consisting of olefin, and vinyl polymers, addition polymers, condensation polymers, carbohydrate polymers, and silicon polymers as represented by polyethylene, polypropylene, polyvinyl acetate, polymethylacrylate, polyisobutylmethacrylate, poly alginate, polyamide and polysilicon. The polymers and procedures for manufacturing them have been described in the art (Coleman et al., *Polymers* 1990, 31, 1187–1231; Roerdink et al., *Drug Carrier Systems* 1989, 9, 57–10; Leong et al., *Adv. Drug Delivery Rev.* 1987, 1, 199–233; Roff et al., *Handbook of Common Polymers* 1971, CRC Press; U.S. Pat. No. 3,992,518).

In another embodiment of the invention, the dosage from comprises a plurality of tiny pills. The tiny time-released pills provide a number of individual doses for providing various time doses for achieving a sustained-release prodrug delivery profile over an extended period of time up to 24 hours. The matrix comprises a hydrophilic polymer selected from the group consisting of a polysaccharide, agar, agarose, natural gum, alkali alginate including sodium alginate, carrageenan, fucoidan, furcellaran, laminaran, hypnea, gum arabic, gum ghatti, gum karaya, grum tragacanth, locust bean gum, pectin, amylopectin, gelatin, and a hydrophilic colloid. The hydrophilic matric comprises a plurality of 4 to 50 tiny pills, each tiny pill comprise a dose population of from 10 ng, 0.5 mg, 1 mg, 1.2 mg, 1.4 mg, 1.6 mg, 5.0 mg etc. The tiny pills comprise a release rate-controlling wall of 0.001 up to 10 mm thickness to provide for the timed release of prodrug. Representative wall forming materials include a triglyceryl ester selected from the group consisting of glyceryl tristearate, glyceryl monostearate, glyceryl dipalmitate, glyceryl laureate, glyceryl didecenoate and glyceryl tridenoate. Other wall forming materials comprise polyvinyl acetate, phthalate, methylcellulose phthalate and microporous olefins. Procedures for manufacturing tiny pills are disclosed in U.S. Pat. Nos. 4,434,153; 4,721,613; 4,853, 229; 2,996,431; 3,139,383 and 4,752,470.

In another embodiment of the invention, the dosage form comprises an osmotic dosage form, which comprises a semipermeable wall that surrounds a therapeutic composition comprising the prodrug. In use within a patient, the osmotic dosage form comprising a homogenous composition imbibes fluid through the semipermeable wall into the dosage form in response to the concentration gradient across the semipermeable wall. The therapeutic composition in the dosage form develops osmotic energy that causes the therapeutic composition to be administered through an exit from the dosage form over a prolonged period of time up to 24 hours (or even in some cases up to 30 hours) to provide controlled and sustained prodrug release. These delivery platforms can provide an essentially zero order delivery profile as opposed to the spiked profiles of immediate release formulations.

In another embodiment of the invention, the dosage form comprises another osmotic dosage form comprising a wall surrounding a compartment, the wall comprising a semipermeable polymeric composition permeable to the passage of fluid and substantially impermeable to the passage of prodrug present in the compartment, a prodrug-containing layer composition in the compartment, a hydrogel push layer composition in the compartment comprising an osmotic formulation for imbibing and absorbing fluid for expanding in size for pushing the prodrug composition layer from the dosage form, and at least one passageway in the wall for releasing the prodrug composition. The method delivers the prodrug by imbibing fluid through the semipermeable wall at a fluid imbibing rate determined by the permeability of the semipermeable wall and the osmotic pressure across the semipermeable wall causing the push layer to expand, thereby delivering the prodrug from the dosage form through the exit passageway to a patient over a prolonged period of time (up to 24 or even 30 hours). The hydrogel layer composition may comprise 10 mg to 1000 mg of a hydrogel such as a member selected from the group consisting of a polyalkylene oxide of 1,000,000 to 8,000,000 which are selected from the group consisting of a polyethylene oxide of 1,000,000 weight-average molecular weight, a polyethylene oxide of 2,000,000 molecular weight, a polyethylene oxide of 4,000,000 molecular weight, a polyethylene oxide of 5,000,000 molecular weight, a polyethylene oxide of 7,000,000 molecular weight and a polypropylene oxide of the 1,000,000 to 8,000,000 weight-average molecular weight; or 10 mg to 1000 mg of an alkali carboxymethylcellulose of 10,000 to 6,000,000 weight average molecular weight, such as sodium carboxymethylcellulose or potassium carboxymethylcellulose. The hydrogel expansion layer comprises 0.0 mg to 350 mg, in present manufacture; 0.1 mg to 250 mg of a hydroxyalkylcellulose of 7,500 to 4,500,00 weight-average molecular weight (e.g., hydroxymethylcellulose, hydroxyethylcellulose, hydroxypropylcellulose, hydroxybutylcellulose or hydroxypentylcellulose) in present manufacture; 1 mg to 50 mg of an osmagent selected from the group consisting of sodium chloride, potassium chloride, potassium acid phosphate, tartaric acid, citric acid, raffinose, magnesium sulfate, magnesium chloride, urea, inositol, sucrose, glucose and sorbitol; 0 to 5 mg of a colorant, such as ferric oxide; 0 mg to 30 mg, in a present manufacture, 0.1 mg to 30 mg of a hydroxypropylalkylcellulose of 9,000 to 225,000 average-number molecular weight, selected from the group consisting of hydroxypropylethylcellulose, hydroxypropypentylcellulose, hydroxypropylmethylcellulose, and hydropropylbutylcellulose; 0.00 to 1.5 mg of an antioxidant selected from the group consisting of ascorbic acid, butylated hydroxyanisole, butylatedhydroxyquinone, butylhydroxyanisol, hydroxycomarin, butylated hydroxytoluene, cephalm, ethyl gallate, propyl gallate, octyl gallate, lauryl gallate, propylhydroxybenzoate, trihydroxybutylrophenone, dimethylphenol, dibutylphenol, vitamin E, lecithin and ethanolamine; and 0.0 mg to 7 mg of a lubricant selected from the group consisting of calcium stearate, magnesium stearate, zinc stearate, magnesium oleate, calcium palmitate, sodium suberate, potassium laureate, salts of fatty acids, salts of alicyclic acids, salts of aromatic acids, stearic acid, oleic acid, palmitic acid, a mixture of a salt of a fatty, alicyclic or aromatic acid, and a fatty, alicyclic, or aromatic acid.

In the osmotic dosage forms, the semipermeable wall comprises a composition that is permeable to the passage of fluid and impermeable to the passage of prodrug. The wall is nontoxic and comprises a polymer selected from the group consisting of a cellulose acylate, cellulose diacylate, cellulose triacylate, cellulose acetate, cellulose diacetate and cellulose triacetate. The wall comprises 75 wt % (weight percent) to 100 wt % of the cellulosic wall-forming polymer; or, the wall can comprise additionally 0.01 wt % to 80 wt % of polyethylene glycol, or 1 wt % to 25 wt % of a cellulose ether selected from the group consisting of hydroxypropylcellulose or a hydroxypropylalkycellulose such as hydroxypropylmethylcellulose. The total weight percent of all components comprising the wall is equal to 100 wt %. The internal compartment comprises the prodrug-containing composition alone or in layered position with an expandable hydrogel composition. The expandable hydrogel composition in the compartment increases in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of prodrug to a patient over time. The dosage form comprises a passageway in the wall that connects the exterior of the dosage form with the internal compartment. The osmotic powered dosage form provided by the invention delivers prodrug from the dosage form to the patient at a zero order rate of release over a period of up to about 24 hours.

The expression "passageway" as used herein comprises means and methods suitable for the metered release of the prodrug from the compartment of the dosage form. The exit means comprises at least one passageway, including orifice, bore, aperture, pore, porous element, hollow fiber, capillary tube, channel, porous overlay, or porous element that provides for the osmotic controlled release of prodrug. The passageway includes a material that erodes or is leached from the wall in a fluid environment of use to produce at least one controlled-release dimensioned passageway. Representative materials suitable for forming a passageway, or a multiplicity of passageways comprise a leachable poly (glycolic) acid or poly(lactic) acid polymer in the wall, a gelatinous filament, poly(vinyl alcohol), leach-able polysaccharides, salts, and oxides. A pore passageway, or more than one pore passageway, can be formed by leaching a leachable compound, such as sorbitol, from the wall. The passageway possesses controlled-release dimensions, such as round, triangular, square and elliptical, for the metered release of prodrug from the dosage form. The dosage form can be constructed with one or more passageways in spaced apart relationship on a single surface or on more than one surface of the wall. The expression "fluid environment"

denotes an aqueous or biological fluid as in a human patient, including the gastrointestinal tract. Passageways and equipment for forming passageways are disclosed in U.S. Pat. Nos. 3,845,770; 3,916,899; 4,063,064; 4,088,864 and 4,816,263. Passageways formed by leaching are disclosed in U.S. Pat. Nos. 4,200,098 and 4,285,987.

Regardless of the specific form of sustained release oral dosage form used, the prodrug is preferably released from the dosage form over a period of at least about 6 hours, more preferably, over a period of at least about 8 hours, and most preferably, over a period of at least about 12 hours. Further, the dosage form preferably releases from 0 to 20% of the prodrug in 0 to 2 hours, from 20 to 50% of the prodrug in 2 to 12 hours, from 50 to 85% of the prodrug in 3 to 20 hours and greater than 75% of the prodrug in 5 to 18 hours. The sustained release oral dosage form further provides a concentration of the GABA analog in the blood plasma of the patient over time, which curve has an area under the curve (AUC) that is proportional to the dose of the prodrug of GABA analog administered, and a maximum concentration $C_{max}$. The $C_{max}$ is less than 75%, and is preferably, less than 60%, of the $C_{max}$ obtained from administering an equivalent dose of the prodrug from an immediate release oral dosage form, and the AUC is substantially the same as the AUC obtained from administering an equivalent dose of the prodrug from an immediate release oral dosage form.

Preferably, the dosage forms of the invention are administered twice per day (more preferably, once per day).

Prodrugs Useful in the Invention

It should be understood that the present invention is not restricted to particular prodrugs of GABA analogs. Accordingly, the present invention may be practiced with any GABA analog prodrug.

One preferred class of GABA analog prodrugs particularly useful in the present invention has the structure of Formula (I):

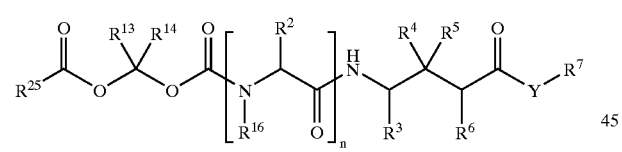

(I)

or a pharmaceutically acceptable salt, hydrate or solvate thereof, wherein:

n is 0 or 1;

Y is O or S;

$R^{16}$ is hydrogen, alkyl or substituted alkyl;

$R^2$ is selected from the group consisting of hydrogen, alkyl, substituted alkyl, alkoxy, substituted alkoxy, acyl, substituted acyl, acylamino, substituted acylamino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy, or optionally, $R^2$ and $R^{16}$ together with the atoms to which they are attached form a cycloheteroalkyl or substituted cycloheteroalkyl ring;

$R^3$ and $R^6$ are independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl;

$R^4$ and $R^5$ are independently selected from the group consisting of hydrogen, alkyl, substituted alkyl, acyl, substituted acyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl and substituted heteroarylalkyl or optionally, $R^4$ and $R^5$ together with the carbon atom to which they are attached form a cycloalkyl, substituted cycloalkyl, cycloheteroalkyl, substituted cycloheteroalkyl or bridged cycloalkyl ring;

$R^7$ is selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

$R^{13}$ and $R^{14}$ are each independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl or substituted heteroarylalkyl or optionally, $R^{13}$ and $R^{14}$ together with the carbon atom to which they are attached form a cycloalkyl, substituted cycloalkyl, cycloheteroalkyl or substituted cycloheteroalkyl ring; and $R^{25}$ is selected from the group consisting of acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl.

Preferably, $R^{13}$ and $R^{14}$ are independently hydrogen, alkyl, substituted alkyl, alkoxycarbonyl, aryl, arylalkyl, carbamoyl, cycloalkyl, substituted cycloalkyl, cycloalkoxycarbonyl or heteroaryl (preferably, when $R^{13}$ is alkoxycarbonyl, cycloalkoxycarbonyl or carbamoyl then $R^{14}$ is methyl). More preferably, $R^{13}$ and $R^{14}$ are independently hydrogen, methyl, ethyl, propyl, isopropyl, butyl, isobutyl, sec-butyl, tert-butyl, cyclopentyl, cyclohexyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclohexyloxycarbonyl, phenyl, benzyl, phenethyl or 3-pyridyl.

In one embodiment, $R^{13}$ and $R^{14}$ are independently hydrogen, alkanyl, substituted alkanyl, cycloalkanyl or substituted cycloalkanyl. Preferably, $R^{13}$ and $R^{14}$ are hydrogen, alkanyl or cycloalkanyl. More preferably, $R^{13}$ and $R^{14}$ are independently hydrogen, methyl, ethyl, propyl, isopropyl, butyl, isobutyl, sec-butyl, tert-butyl, cyclopentyl or cyclohexyl. Even more preferably, $R^{13}$ is methyl, ethyl, propyl, isopropyl, butyl, isobutyl, sec-butyl, tert-butyl, cyclopentyl or cyclohexyl and $R^{14}$ is hydrogen, or $R^{13}$ is methyl and $R^{14}$ is methyl.

In another embodiment, $R^{13}$ and $R^{14}$ are independently hydrogen, aryl, arylalkyl or heteroaryl. More preferably, $R^{13}$ and $R^{14}$ are independently hydrogen, phenyl, benzyl, phenethyl or 3-pyridyl. Even more preferably, $R^{13}$ is phenyl, benzyl, phenethyl or 3-pyridyl and $R^{14}$ is hydrogen.

In still another embodiment, $R^{13}$ and $R^{14}$ are independently, alkyl, substituted alkyl, alkoxycarbonyl, carbamoyl, or cycloalkoxycarbonyl. Preferably, when $R^{13}$ is alkoxycarbonyl, cycloalkoxycarbonyl or carbamoyl then $R^{14}$ is methyl. More preferably, $R^{13}$ is methoxycarbonyl, ethoxycarbonyl, isopropoxycarbonyl, butoxycarbonyl, isobutoxycarbonyl, sec-butoxycarbonyl, tert-butoxycarbonyl or cyclohexyloxycarbonyl and $R^{14}$ is methyl.

In still another embodiment, $R^{13}$ and $R^{14}$ together with the carbon atom to which they are attached form a cycloalkyl, substituted cycloalkyl, cycloheteroalkyl or substituted cycloheteroalkyl ring. Preferably, $R^{13}$ and $R^{14}$ together with the carbon atom to which they are attached form a cycloalkyl ring. More preferably, $R^{13}$ and $R^{14}$ together with the carbon atom to which they are attached form a cyclobutyl, cyclopentyl or cyclohexyl ring.

In still another preferred embodiment of compounds of Formula (I), $R^{25}$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl;

$R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl or $R^{13}$ and $R^{14}$ together with the carbon atom to which they are attached form a cycloalkyl, substituted cycloalkyl, cycloheteroalkyl or substituted cycloheteroalkyl ring. Preferably, $R^{25}$ is acyl, substituted acyl, alkyl, substituted alkyl, aryl, arylalkyl, cycloalkyl or heteroaryl. More preferably, $R^{25}$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

In still another embodiment, $R^{25}$ is acyl or substituted acyl. More preferably, $R^{25}$ is acetyl, propionyl, butyryl, benzoyl or phenacetyl.

In still another embodiment, $R^{25}$ is alkanyl or substituted alkanyl. Preferably, $R^{25}$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl or 1-(1,3-dioxan-2-yl)-2-phenethyl. More preferably, $R^{25}$ is methyl, ethyl, propyl, isopropyl, butyl, 1,1-dimethoxyethyl or 1,1-diethoxyethyl.

In still another embodiment, $R^{25}$ is aryl, arylalkyl or heteroaryl. Preferably, $R^{25}$ is phenyl, 4-methoxyphenyl, benzyl, phenethyl, styryl or 3-pyridyl.

In still another embodiment, $R^{25}$ is cycloalkyl or substituted cycloalkyl. More preferably $R^{25}$ is cyclopropyl, cyclobutyl, cyclopentyl or cyclohexyl.

In still another embodiment of compounds of Formula (I), $R^{25}$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl, and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, substituted alkoxycarbonyl, cycloalkoxycarbonyl, substituted cycloalkoxycarbonyl or carbamoyl then $R^{14}$ is methyl). Preferably, $R^{25}$ is acyl, substituted acyl, alkyl, substituted alkyl, aryl, arylalkyl, cycloalkyl or heteroaryl and $R^{13}$ and $R^{14}$ are independently hydrogen, alkyl, substituted alkyl, alkoxycarbonyl, aryl, arylalkyl, carbamoyl, cycloalkyl, cycloalkoxycarbonyl or heteroaryl (preferably, when $R^{13}$ is alkoxycarbonyl, substituted alkoxycarbonyl, cycloalkoxycarbonyl, substituted cycloalkoxycarbonyl or carbamoyl then $R^{14}$ is methyl). More preferably, $R^{25}$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl, and $R^{13}$ and $R^{14}$ are independently hydrogen, methyl, ethyl, propyl, isopropyl, butyl, isobutyl, sec-butyl, tert-butyl, cyclopentyl, cyclohexyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclohexyloxycarbonyl, phenyl, benzyl, phenethyl or 3-pyridyl. Even more preferably, $R^{25}$ is methyl, ethyl, propyl, isopropyl, butyl, isobutyl, sec-butyl, 1,1-dimethoxyethyl, 1,1-diethoxyethyl, 1,1-dimethoxybenzyl, 1,1-diethoxybenzyl, 1,1-dimethoxy-2-phenethyl, 1,1-diethoxy-2-phenethyl, acetyl, propionyl, butyryl, benzoyl, phenacetyl, phenyl, 4-methoxyphenyl, benzyl, phenethyl, cyclohexyl or 3-pyridyl, and $R^{13}$ and $R^{14}$ are independently hydrogen, methyl, ethyl, propyl, isopropyl, butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl or 3-pyridyl.

In still another embodiment, $R^{25}$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl, and $R^{13}$ and $R^{14}$ together with the atom to which they are attached form a cycloalkyl, substituted cycloalkyl, cycloheteroalkyl or substituted cycloheteroalkyl ring. Preferably, $R^{25}$ is acyl, substituted acyl, alkyl, substituted alkyl, aryl, arylalkyl, cycloalkyl or heteroaryl and $R^{13}$ and $R^{14}$ together with the atom to which they are attached form a cycloalkyl or substituted cycloalkyl ring. More preferably, $R^{25}$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl, and $R^{13}$ and $R^{14}$ together with the atom to which they are attached form a cyclobutyl, cyclopentyl or a cyclohexyl ring.

In still another embodiment, $R^{25}$ is acyl or substituted acyl and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, substituted alkoxycarbonyl, cycloalkoxycarbonyl, substituted cycloalkoxycarbonyl or carbamoyl then $R^{14}$ is methyl). Preferably, $R^{25}$ is acetyl, propionyl, butyryl, benzoyl or phenacetyl, and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, cycloalkoxycarbonyl or carbamoyl then $R^{14}$ is methyl).

In still another preferred embodiment, $R^{25}$ is alkanyl or substituted alkanyl and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, substituted alkoxycarbonyl, cycloalkoxycarbonyl, substituted cycloalkoxycarbonyl or carbamoyl then $R^{14}$ is methyl). Preferably, $R^{25}$ is methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1, 3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl or 1-(1,3-dioxan-2-yl)-2-phenethyl, and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, cycloalkoxycarbonyl or carbamoyl then $R^{14}$ is methyl).

In still another embodiment, $R^{25}$ is aryl, substituted aryl, arylalkyl, substituted arylalkyl, heteroaryl or substituted heteroaryl, and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, substituted alkoxycarbonyl, cycloalkoxycarbonyl, substituted cycloalkoxycarbonyl or carbamoyl then $R^{14}$ is methyl). Preferably $R^{25}$ is phenyl, 4-methoxyphenyl, benzyl, phenethyl, styryl or 3-pyridyl and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, cycloalkoxycarbonyl or carbamoyl then $R^{14}$ is methyl).

In still another embodiment, $R^{25}$ is cycloalkyl or substituted cycloalkyl, and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, substituted alkoxycarbonyl, cycloalkoxycarbonyl, substituted cycloalkoxycarbonyl or carbamoyl then $R^{14}$ is methyl). Preferably, $R^{25}$ is cyclopropyl, cyclobutyl, cyclopentyl or cyclohexyl and $R^{13}$ and $R^{14}$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl (preferably, when $R^{13}$ is alkoxycarbonyl, cycloalkoxycarbonyl or carbamoyl then $R^{14}$ is methyl).

In still another embodiment, $R^{25}$ is acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl, and $R^{13}$ and $R^{14}$ are independently hydrogen, alkyl, substituted alkyl, aryl, arylalkyl, cycloalkyl or heteroaryl. Preferably, $R^{25}$ is acyl, substituted acyl, alkyl, substituted alkyl, aryl, arylalkyl, cycloalkyl or heteroaryl and $R^{13}$ and $R^{14}$ are independently hydrogen, alkanyl, substituted alkanyl, cycloalkanyl or substituted cycloalkanyl. More preferably, $R^{25}$ is acyl, substituted acyl, alkyl, substituted alkyl, aryl, arylalkyl, cycloalkyl or heteroaryl and $R^{13}$ and $R^{14}$ are independently hydrogen, methyl, ethyl, propyl, isopropyl, butyl, isobutyl, sec-butyl, tert-butyl, cyclopentyl or cyclohexyl. In the above embodiments, $R^{25}$ is preferably methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

In still another embodiment, $R^{25}$ is acyl, substituted acyl, alkyl, substituted alkyl, aryl, arylalkyl, cycloalkyl or heteroaryl and $R^{13}$ and $R^{14}$ are independently hydrogen, alkyl, substituted alkyl, aryl, arylalkyl, cycloalkyl or heteroaryl. Preferably, $R^{25}$ is acyl, substituted acyl, alkyl, substituted alkyl, aryl, arylalkyl, cycloalkyl or heteroaryl and $R^{13}$ and $R^{14}$ are independently hydrogen, aryl, arylalkyl or heteroaryl. More preferably, $R^{25}$ is acyl, substituted acyl, alkyl, substituted alkyl, aryl, arylalkyl, cycloalkyl or heteroaryl and $R^{13}$ and $R^{14}$ are independently hydrogen, phenyl, benzyl, phenethyl or 3-pyridyl. In the above embodiments, $R^{25}$ is preferably methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

In still another embodiment, $R^{25}$ is acyl, substituted acyl, alkyl, substituted alkyl, aryl, arylalkyl, cycloalkyl or heteroaryl and $R^{13}$ and $R^{14}$ are independently hydrogen, alkyl, substituted alkyl, aryl, arylalkyl, cycloalkyl or heteroaryl. Preferably, $R^{25}$ is acyl, substituted acyl, alkyl, substituted alkyl, aryl, arylalkyl, cycloalkyl or heteroaryl and $R^{14}$ are independently hydrogen, alkyl, substituted alkyl, alkoxycarbonyl, substituted alkoxycarbonyl, carbamoyl, cycloalkoxycarbonyl or substituted cycloalkoxycarbonyl (preferably, when $R^{13}$ is alkoxycarbonyl, substituted alkoxycarbonyl, carbamoyl, cycloalkoxycarbonyl or substituted cycloalkoxycarbonyl then $R^{14}$ is methyl, more preferably, $R^{13}$ is methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl or cyclohexyloxycarbonyl, and $R^{14}$ is methyl). In the above embodiments, $R^{25}$ is preferably methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1, 3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

In still another preferred embodiment, $R^{25}$ is acyl, substituted acyl, alkyl, substituted alkyl, aryl, arylalkyl, cycloalkyl or heteroaryl and $R^{13}$ and $R^{14}$ together with the atom to which they are attached form a cycloalkyl, substituted cycloalkyl, cycloheteroalkyl or substituted cycloheteroalkyl ring. Preferably, $R^{25}$ is acyl, substituted acyl, alkyl, substituted alkyl, aryl, arylalkyl, cycloalkyl or heteroaryl and $R^{13}$ and $R^{14}$ together with the atom to which they are attached form a cycloalkyl or substituted cycloalkyl ring. More preferably $R^{25}$ is acyl, substituted acyl, alkyl, substituted alkyl, aryl, arylalkyl, cycloalkyl or heteroaryl, and $R^{13}$ and $R^{14}$ together with the atom to which they are attached form a cyclobutyl, cyclopentyl or cyclohexyl ring. In the above embodiments, $R^{25}$ is preferably methyl, ethyl, propyl, isopropyl, butyl, isobutyl, sec-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl or 3-pyridyl.

In still another preferred embodiment of compounds of Formula (I), $R^4$ and $R^5$ together with the carbon atom to which they are attached form a cyclobutyl or substituted cyclobutyl ring. Preferably, the substituted cyclobutyl ring is substituted with one or more substituents selected from the group consisting of alkanyl, substituted alkanyl, halo, hydroxy, carboxy and alkoxycarbonyl.

In still another preferred embodiment of compounds of Formula (I), $R^4$ and $R^5$ together with the carbon atom to which they are attached form a cyclopentyl or substituted cyclopentyl ring. Preferably, the cyclopentyl ring is substituted with alkanyl, substituted alkanyl, halo, hydroxy, carboxy or alkoxycarbonyl. More preferably, the cyclopentyl ring is substituted with alkanyl. Even more preferably, the cyclopentyl ring is selected from the group consisting of

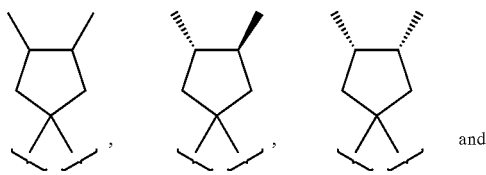

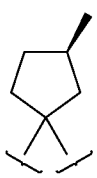

Preferably, in a more specific version of this embodiment, $R^7$ is hydrogen.

In still another preferred embodiment of compounds of formula (IV), $R^4$ and $R^5$ together with the carbon atom to which they are attached form a cyclohexyl or substituted cyclohexyl ring. Preferably, the cyclohexyl ring is substituted with alkanyl, substituted alkanyl, halo, hydroxy, carboxy or alkoxycarbonyl. More preferably, the cyclohexyl ring is substituted with alkanyl. Even more preferably, the cyclohexyl ring is selected from the group consisting of

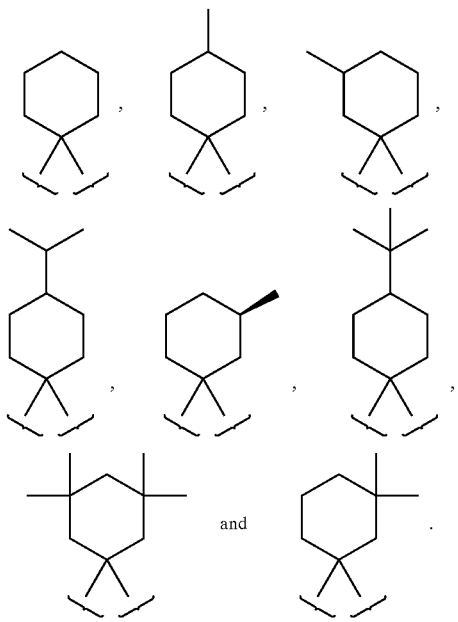

Preferably, in a more specific version of this embodiment, $R^7$ is hydrogen.

In still another preferred embodiment of compounds of Formula (I), $R^4$ and $R^5$ together with the carbon atom to which they are attached form a cycloheteroalkyl or substituted cycloheteroalkyl ring. In one embodiment, n is 0. In another embodiment, n is 1, and $R^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, CH$_2$SH, —CH$_2$(CH$_2$)$_3$NH$_2$ or —CH$_2$CH$_2$NHC(NH)NH$_2$. In another embodiment, n is 1 and $R^2$ $R^{16}$ together with the atoms to which they are attached form a pyrrolidine ring. Preferably, $R^4$ and $R^5$ together with the carbon atom to which they are attached form a cycloheteroalkanyl ring. More preferably, the cycloheteroalkanyl ring is selected from the group consisting of

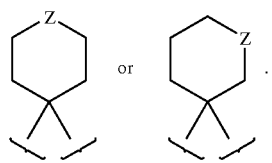

wherein Z is O, S(O)$_p$ or NR$^{18}$;
p is 0, 1 or 2; and
$R^{18}$ is selected from the group consisting of hydrogen, alkyl, substituted alkyl, acyl and alkoxycarbonyl. More preferably, the cycloheteroalkanyl ring is selected from the group consisting of

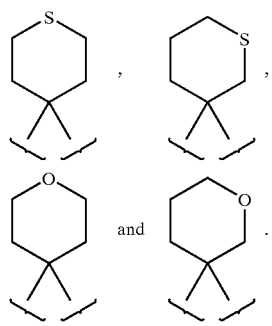

Preferably, in a more specific version of this embodiment, $R^7$ is hydrogen.

In still another embodiment of compounds of Formula (I), $R^4$ and $R^5$ together with the carbon atom to which they are attached form a bridged cycloalkyl ring. In one embodiment, n is 0. In another embodiment, n is 1 and $R^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, CH$_2$SH, —CH$_2$(CH$_2$)$_3$NH$_2$ or —CH$_2$CH$_2$CH$_2$NHC(NH)NH$_2$. In another embodiment, n is 1 and $R^2$ and $R^{16}$ together with the atoms to which they are attached form a pyrrolidine ring. Preferably, the bridged cycloalkyl group is

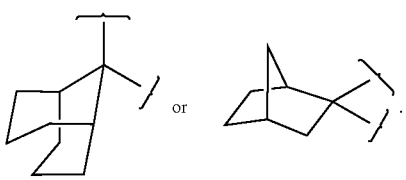

Preferably, in a more specific version of this embodiment, $R^7$ is hydrogen.

In still another embodiment of compounds of Formula (I), Y is O, $R^6$ and $R^7$ are hydrogen, $R^4$ is alkyl or cycloalkyl, $R^5$ is hydrogen or alkyl and $R^3$ is hydrogen or alkyl. In one embodiment, n is 0. In another embodiment, n is 1 and $R^2$ is hydrogen, methyl, 2-propyl, 2-butyl, isobutyl, t-butyl, cyclopentyl, cyclohexyl, phenyl, benzyl, 4-hydroxybenzyl, 2-imidazolyl, 2-indolyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, CH$_2$SH, —CH$_2$(CH$_2$)$_3$NH$_2$ or —CH$_2$CH$_2$CH$_2$NHC(NH)NH$_2$. In another embodiment, n is 1 and $R^2$ and $R^{16}$ together with the atoms to which they are attached form a pyrrolidine ring.

Preferably, $R^4$ is cycloalkyl, $R^5$ is hydrogen or methyl, and $R^3$ is hydrogen or methyl. Preferably, $R^3$ is hydrogen, $R^4$ is isobutyl and $R^5$ is hydrogen.

In still another embodiment of compounds of Formula (I), Y is O, $R^5$ and $R^7$ are hydrogen or alkanyl, $R^3$ and $R^6$ are hydrogen and $R^4$ is substituted heteroalkyl. Preferably, $R^4$ is

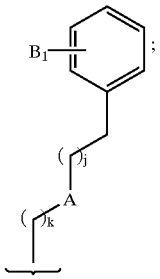

A is $NR^{19}$, O or S;

B is alkyl, substituted alkyl, alkoxy, halogen, hydroxy, carboxy, alkoxycarbonyl or amino;

$R^{19}$ is hydrogen, alkyl, cycloalkyl or aryl;

j is an integer from 0 to 4;

k is an integer from 1 to 4; and l is an integer from 0 to 3.

More preferably, k is 1.

In still another embodiment of compounds of Formula (I), Y is O, $R^5$ and $R^7$ are hydrogen or alkanyl, $R^3$ and $R^6$ are hydrogen and $R^4$ is substituted alkanyl, cycloalkanyl or substituted cycloalkanyl. Preferably, $R^4$ is selected from the group consisting of

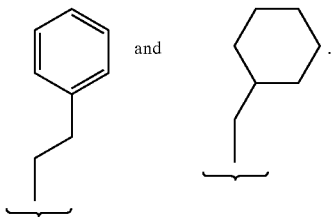

Preferably, $R^4$ is

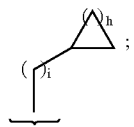

h is an integer from 1 to 6; and i is an integer from 0 to 6.

More preferably, h is 1, 2, 3 or 4 and i is 0 or 1. Even more preferably, $R^4$ is selected from the group consisting of

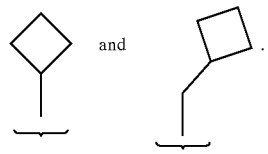

Preferably, compounds of Formula (I) are derived from a GABA analog of Formula (IV):

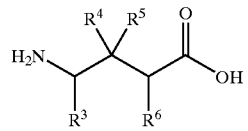

wherein the GABA analog of Formula (IV) is selected from the group consisting of:

1-Aminomethyl-1-cyclohexane acetic acid;
1-Aminomethyl-1-(3-methylcyclohexane) acetic acid;
1-Aminomethyl-1-(4-methylcyclohexane) acetic acid;
1-Aminomethyl-1-(4-isopropylcyclohexane) acetic acid;
1-Aminomethyl-1-(4-tert-butylcyclohexane) acetic acid;
1-Aminomethyl-1-(3,3-dimethylcyclohexane) acetic acid;
1-Aminomethyl-1-(3,3,5,5-tetramethylcyclohexane) acetic acid;
1-Aminomethyl-1-cyclopentane acetic acid;
1-Aminomethyl-1-(3-methylcyclopentane) acetic acid;
1-Aminomethyl-1-(3,4-dimethylcyclopentane) acetic acid;
7-Aminomethyl-bicyclo[2.2.1]hept-7-yl acetic acid;
9-Aminomethyl-bicyclo[3.3.1]non-9-yl acetic acid;
4-Aminomethyl-4-(tetrahydropyran-4-yl) acetic acid;
3-Aminomethyl-3-(tetrahydropyran-3-yl) acetic acid;
4-Aminomethyl-4-(tetrahydrothiopyran-4-yl) acetic acid;
3-Aminomethyl-3-(tetrahydrothiopyran-3-yl) acetic acid;
3-Aminomethyl-5-methyl-hexanoic acid;
3-Aminomethyl-5-methyl-heptanoic acid;
3-Aminomethyl-5-methyl-octanoic acid;
3-Aminomethyl-5-methyl-nonanoic acid;
3-Aminomethyl-5-methyl-decanoic acid;
3-Aminomethyl-5-cyclopropyl-hexanoic acid;
3-Aminomethyl-5-cyclobutyl-hexanoic acid;
3-Aminomethyl-5-cyclopentyl-hexanoic acid;
3-Aminomethyl-5-cyclohexyl-hexanoic acid;
3-Aminomethyl-5-phenyl-hexanoic acid;
3-Aminomethyl-5-phenyl-pentanoic acid;
3-Aminomethyl-4-cyclobutyl-butynic acid;
3-Aminomethyl-4-cyclopentyl-butyric acid;
3-Aminomethyl-4-cyclohexyl-butyric acid;
3-Aminomethyl-4-phenoxy-butyric acid;
3-Aminomethyl-5-phenoxy-hexanoic acid; and
3-Aminomethyl-5-benzylsulfanyl-pentanoic acid.

In a preferred embodiment, compounds of Formula (I) have the structure of Formulae (II) and (III):

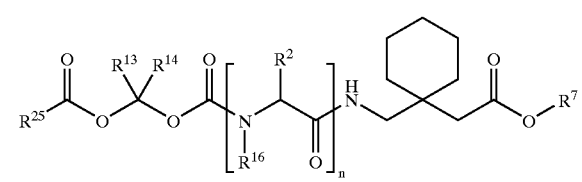

-continued

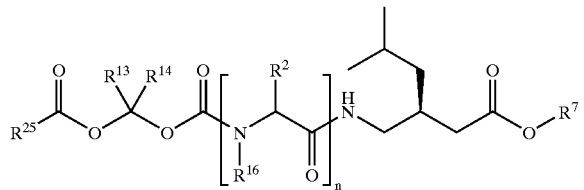

(III)

and a pharmaceutically acceptable salt, hydrate or solvate thereof, wherein:

n, $R^2$, $R^7$, $R^{13}$, $R^{14}$, $R^{16}$ and $R^{25}$ are as previously defined.

In one preferred embodiment of compounds of Formulae (II) and (III), n is 0. In another embodiment, n is 1. When n is 1, preferably the α-amino acid is of the L-stereochemical configuration.

In one embodiment of compounds of Formulae (II) and (III), $R^7$ is hydrogen, alkanyl, substituted alkanyl, alkenyl, substituted alkenyl, aryl or substituted aryl. More preferably, $R^7$ is H, —C(CH₃)=CH₂, —CH₂C(O)N(CH₃)₂,

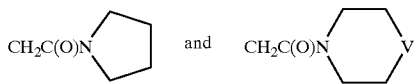

where V is O or CH₂.

Most preferably, $R^7$ is hydrogen.

In one embodiment of compounds of Formulae (II) and (III), n is 0. In another embodiment of compounds of Formulae (II) and (III), n is 1, $R^{16}$ is hydrogen and $R^2$ is hydrogen, methyl, 2-propyl, 2-butyl, isobutyl, tert-butyl, cyclopentyl, cyclohexyl, phenyl, benzyl, 4-hydroxybenzyl, 2-imidazolyl, 2-indolyl, —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂ or —CH₂CH₂CH₂NHC(NH)NH₂. More preferably $R^{16}$ is hydrogen and $R^2$ is hydrogen, methyl, 2-propyl, 2-butyl, isobutyl, tert-butyl, cyclohexyl, phenyl or benzyl. In another embodiment, n is 1 and $R^2$ and $R^{16}$ together with the atoms to which they are attached form a pyrrolidine ring.

In still another embodiment, of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is hydrogen and $R^{14}$ is hydrogen.

In still another embodiment, of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is methyl and $R^{14}$ is hydrogen.

In still another embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is ethyl and $R^{14}$ is hydrogen.

In still another embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is propyl and $R^{14}$ is hydrogen.

In still another preferred embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is isopropyl and $R^{14}$ is hydrogen.

In still another preferred embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3- dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is butyl and $R^{14}$ is hydrogen.

In still another preferred embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is isobutyl and $R^{14}$ is hydrogen.

In still another preferred embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is sec-butyl and $R^{14}$ is hydrogen.

In still another preferred embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is tert-butyl and $R^{14}$ is hydrogen.

In still another embodiment, of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is cyclopentyl and $R^{14}$ is hydrogen.

In still another embodiment, of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is cyclohexyl and $R^{14}$ is hydrogen.

In still another embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is methyl and $R^{14}$ is methyl.

In still another embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is methoxycarbonyl and $R^{14}$ is methyl.

In still another embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is ethoxycarbonyl and $R^{14}$ is methyl.

In still another embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is propoxycarbonyl and $R^{14}$ is methyl.

In still another embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is isopropoxycarbonyl and $R^{14}$ is methyl.

In still another embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is butoxycarbonyl and $R^{14}$ is methyl.

In still another embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is isobutoxycarbonyl and $R^{14}$ is methyl.

In still another embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is sec-butoxycarbonyl and $R^{14}$ is methyl.

In still another embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is tert-butoxycarbonyl and $R^{14}$ is methyl.

In still another embodiment of compounds of Formulae (II) and (III), is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is cyclohexyloxycarbonyl and $R^{14}$ is methyl.

In still another embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is phenyl and $R^{14}$ is hydrogen.

In still another embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is benzyl and $R^{14}$ is hydrogen.

In still another embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is phenethyl and $R^{14}$ is hydrogen.

In still another embodiment of compounds of Formulae (II) and (III), $R^{25}$ is selected from the group consisting of methyl, ethyl, propyl, isopropyl, butyl, isobutyl, sec-butyl, tert-butyl, pentyl, isopentyl, sec-pentyl, neopentyl, 1,1-dimethoxyethyl, 1,1-diethoxyethyl, 1-(1,3-dioxolan-2-yl)-ethyl, 1-(1,3-dioxan-2-yl)-ethyl, 1,1-dimethoxypropyl, 1,1-diethoxypropyl, 1-(1,3-dioxolan-2-yl)-propyl, 1-(1,3-dioxan-2-yl)-propyl, 1,1-dimethoxybutyl, 1,1-diethoxybutyl, 1-(1,3-dioxolan-2-yl)-butyl, 1-(1,3-dioxan-2-yl)-butyl, 1,1-dimethoxybenzyl, 1,1-diethoxybenzyl, 1-(1,3-dioxolan-2-yl)-benzyl, 1-(1,3-dioxan-2-yl)-benzyl, 1,1-dimethoxy-2-phenethyl, 1,1-diethoxy-2-phenethyl, 1-(1,3-dioxolan-2-yl)-2-phenethyl, 1-(1,3-dioxan-2-yl)-2-phenethyl, phenethyl, acetyl, propionyl, butyryl, benzoyl, phenacetyl, phenyl, 4-methoxyphenyl, benzyl, phenethyl, styryl, cyclopropyl, cyclobutyl, cyclopentyl, cyclohexyl and 3-pyridyl, $R^{13}$ is 3-pyridyl and $R^{14}$ is hydrogen.

In a preferred embodiment, prodrugs of GABA analogs that are useful in practicing the current invention are those disclosed in the art (Bryans et al., International Publication No. WO 01/90052; U.K. Application GB 2,362,646; European Applications EP 1,201,240 and 1,178,034; Yatvin et al., U.S. Pat. No. 6,024,977; Mulvihill et al., International Publication No. WO 01/544881; Gallop et al, International Publication No. WO 02/42414). In a particularly preferred embodiment, prodrugs of GABA analogs that are useful in practicing the current invention are those disclosed by Bryans et al., International Publication No. WO 01/90052. In one embodiment, preferred prodrugs of GABA analogs include, but are not limited to, [1-(acetoxymethoxycarbonylaminomethyl)-cyclohexyl]-acetic acid; [1-(acetoxymethoxycarbonylaminomethyl)-cyclohexyl]-acetic acid ethyl ester; 2,2-dimethylpropionic acid 1-carboxymethylcyclohexylmethyl-carbamoyloxymethyl ester; 2,2-dimethylpropionic acid 1-ethoxycarbonylmethylcyclohexylmethyl-carbamoyloxymethyl ester; benzoic acid 1-carboxymethyl-cyclohexylmethylcarbamoyloxymethyl ester; and benzoic acid 1-ethoxycarbonlymethyl-cyclohexylmethylcarbamoyloxymethyl ester. In another embodiment, preferred prodrugs of GABA analogs include, but are not limited to, gabapentin and pregabalin peptide derivatives wherein the amino group of the GABA analog is acylated with particular α-aminoacyl or dipeptide moieties. More specifically, the α-amino acids comprising these peptide prodrug derivatives are the 20 naturally encoded α-amino acids, plus phenylglycine.

Synthesis of the Prodrugs Used in the Invention

The prodrugs useful in the invention may be obtained via the synthetic methods illustrated in Schemes 1–5. Those of skill in the art will appreciate that a preferred synthetic route to the compounds of the invention will consist of attaching promoieties to GABA analogs. Numerous methods have been described in the art for the synthesis of GABA analogs (See, e.g., Satzinger et al., U.S. Pat. No. 4,024,175; Silverman et al., U.S. Pat. No. 5,563,175; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Publication No. WO 92/09560; Silverman et al., International Publication No. WO 93/23383; Horwell et al., International Publication No. WO 97/29101, Horwell et al., International Publication No. WO 97/33858; Horwell et al., International Publication No. WO 97/33859; Bryans et al., International Publication No. WO 98/17627; Guglietta et al., International Publication No. WO 99/08671; Bryans et al., International Publication No. WO 99/21824; Bryans et al., International Publication No. WO 99/31057; Belliotti et al., International Publication No. WO 99/31074; Bryans et al., International Publication No. WO 99/31075; Bryans et al., International Publication No. WO 99/61424; Bryans et al., International Publication No. WO 00/15611; Bryans, International Publication No. WO 00/31020; and Bryans et al., International Publication No. WO 00/50027). Other methods are known in the art for synthesizing GABA analogs, which are readily accessible to the skilled artisan. The promoieties described herein, are known in the art and may be prepared and attached to GABA analogs by established procedures (See e.g., Green et al., "Protective Groups in Organic Chemistry", (Wiley, 2$^{nd}$ ed. 1991); Harrison et al., "Compendium of Synthetic Organic Methods", Vols. 1–8 (John Wiley and Sons, 1971–1996); "Beilstein Handbook of Organic Chemistry," Beilstein Institute of Organic Chemistry, Frankfurt, Germany; Feiser et al., "Reagents for Organic Synthesis," Volumes 1–17, Wiley Interscience; Trost et al., "Comprehensive Organic Synthesis," Pergamon Press, 1991; "Theilheimer's Synthetic Methods of Organic Chemistry," Volumes 1–45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995, Bodanzsky, "Principles of Peptide Synthesis," Springer Verlag, 1984; Bodanzsky, "Practice of Peptide Synthesis," Springer Verlag, 1984).

Accordingly, starting materials useful for preparing compounds used in the invention and intermediates thereof are commercially available or can be prepared by well-known synthetic methods. Other methods for synthesis of the prodrugs described herein are either described in the art or will be readily apparent to the skilled artisan in view of the references provided above and may be used to synthesize the compounds of the invention. Accordingly, the methods presented in the Schemes herein are illustrative rather than comprehensive.

In any of the Schemes below, after the amino group of a GABA analog has been functionalized with a promoiety or other protecting group, the carboxylic acid group may be converted to an ester or thioester by many synthetic methods, which are well-known to the skilled artisan. In one preferred embodiment, GABA analogs may be reacted with an alcohol or thiol in the presence of a coupling reagent (e.g., carbodiimide and dimethylamino pyridine) to provide the ester. In another preferred embodiment, GABA analogs may be reacted with an alkyl halide in the presence of base to yield the ester. Other methods for converting GABA analogs to esters or thioesters are well within the purview of the skilled artisan in view of the references provided herein.

One method for synthesis of compounds of Formula (I) is illustrated in Scheme 1.

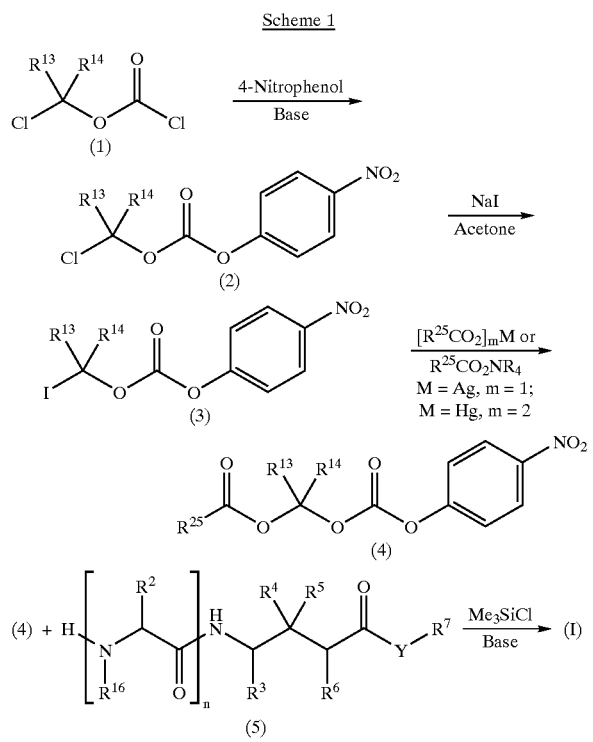

Chloroformate (1) is treated with an aromatic leaving group such as p-nitrophenol in the presence of base to provide p-nitrophenylcarbonate (2). Halide interchange provides iodide (3), which is reacted with a metal or tetraalkylammonium salt of a carboxylic acid to afford compound (4). Treatment of (4) with GABA derivative (5), optionally in the presence of trimethylsilyl chloride, affords a compound of Formula (I). Methods for making related acyloxyalkyl carbamate compounds have been described in the art (Alexander, U.S. Pat. No. 4,760,057; Alexander, U.S. Pat. No. 4,916,230; Alexander, U.S. Pat. No. 5,466,811; Alexander, U.S. Pat. No. 5,684,018).

Alternatively compounds of Formula (I) can be prepared from carbonate (4) in a stepwise fashion as illustrated in Scheme 2. Here reaction of (4) with an α-amino acid (6), optionally protected as a carboxylate ester, affords intermediate (7) which upon deprotection (if necessary) provides compound (8), which is then coupled to GABA analog (9) using standard peptide coupling reagents well known in the art.

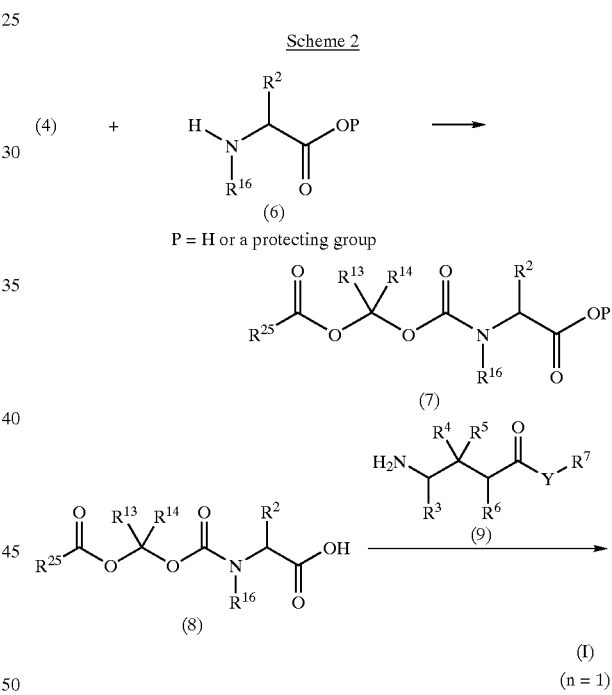

Another method for synthesis of compounds of Formula (I) proceeds via carbonylation of GABA analog derivative (5) to an intermediate carbamic acid species, which is captured by an in situ alkylation reaction in an adaptation of the methods disclosed in the art (Butcher, *Synlett*, 1994, 825–6; and Ferres et al., U.S. Pat. No. 4,036,829). Carbon dioxide gas is bubbled into a solution containing (5) and a base (e.g., $Cs_2CO_3$, $Ag_2CO_3$ or AgO) in a solvent such as DMF or NMP. The activated halide is added, optionally in the presence of iodide ion as a catalyst, and the carbonylation continued until the reaction is completed. This method is illustrated in Scheme 3 for the preparation of compounds of Formula (I) from halide (10).

Scheme 3

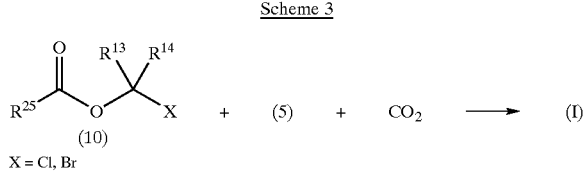

Alternatively compounds of Formula (I) can be prepared in a stepwise fashion as illustrated in Scheme 4. Carbonylation and alkylation of carboxyl protected α-amino acid (6) provides intermediate (7), which upon deprotection is coupled to GABA analog (9) as previously described in Scheme 2.

Scheme 4

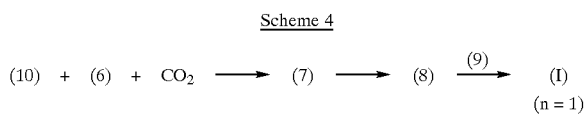

Yet another method for synthesis of compounds of Formula (I) relies upon oxidation of ketocarbamate derivatives of GABA analogs (Gallop et al., U.S. patent application Ser. No. 10/167,797 entitled "Methods for Synthesis of Prodrugs from 1-Acyl-Alkyl Derivatives and Compositions Thereof"). As illustrated in Scheme 5, oxidation of ketocarbamate (11) affords compounds of Formula (I). Preferred solvents include, but are not limited to, t-butanol, diethylether, acetic acid, hexane, dichloroethane, dichloromethane, ethyl acetate, acetonitrile, methanol, chloroform and water. Generally, the oxidant may be an organism (e.g., yeast or bacteria), or a chemical reagent (e.g., an enzyme or peroxide). Preferred oxidants include those, which have been successfully used in Baeyer-Villager oxidations of ketones to esters or lactones (Strukul, *Angnew. Chem. Int. Ed.*, 1998, 37, 1198; Renz et al., *Eur. J. Org. Chem.* 1999, 737; Beller et al., in "Transition Metals in Organic Synthesis" Chapter 2, Wiley VCH; Stewart, *Current Organic Chemistry*, 1998, 2, 195; Kayser et al., *Synlett*, 1999, 1, 153).

Scheme 5

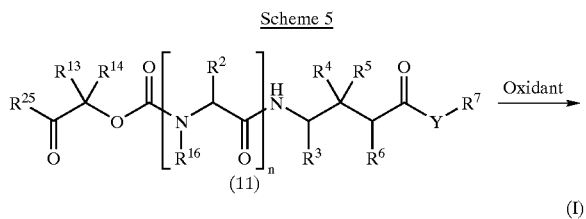

Therapeutic Uses of the Dosage Forms of the Invention

In accordance with the invention, an extended release oral dosage form of the invention is administered to a patient, preferably a human, suffering from epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders or ethanol withdrawal syndrome. Further, in certain embodiments, the dosage forms of the invention are administered to a patient, preferably a human, as a preventative measure against various diseases or disorders. Thus, the dosage forms of the invention may be administered as a preventative measure to a patient having a predisposition for epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders and ethanol withdrawal syndrome. Accordingly, the dosage forms of the invention may be used for the prevention of one disease or disorder and concurrently treating another (e.g., prevention of psychosis while treating gastrointestinal disorders; prevention of neuropathic pain while treating ethanol withdrawal syndrome).

The suitability of the dosage forms of the invention in treating epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders and ethanol withdrawal syndrome may be determined by methods described in the art (See, e.g., Satzinger et al., U.S. Pat. No. 4,024,175; Satzinger et al., U.S. Pat. No. 4,087,544; Woodruff, U.S. Pat. No. 5,084,169; Silverman et al., U.S. Pat. No. 5,563,175; Singh, U.S. Pat. No. 6,001,876; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Publication No. WO 92/09560; Silverman et al., International Publication No. WO 93/23383; Horwell et al., International Publication No. WO 97/29101, Horwell et al., International Publication No. WO 97/33858; Horwell et al., International Publication No. WO 97/33859; Bryans et al., International Publication No. WO 98/17627; Guglietta et al., International Publication No. WO 99/08671; Bryans et al., International Publication No. WO 99/21824; Bryans et al., International Publication No. WO 99/31057; Magnus-Miller et al., International Publication No. WO 99/37296; Bryans et al., International Publication No. WO 99/31075; Bryans et al., International Publication No. WO 99/61424; Pande, International Publication No. WO 00/23067; Bryans, International Publication No. WO 00/31020; Bryans et al., International Publication No. WO 00/50027; and Bryans et al, International Publication No. WO 02/00209). The dosage forms of the invention may be used to treat or prevent epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders and ethanol withdrawal syndrome by procedures described in the art (see references above). Thus, it is well with the capability of those of skill in the art to assay and use the dosage forms of the invention to treat or prevent epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders and ethanol withdrawal syndrome.

Therapeutic/Prophylactic Administration

The dosage forms of the invention may be advantageously used in human medicine. As previously described, the dosage forms of the invention are useful for the treatment or prevention of epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders or ethanol withdrawal syndrome.

When used to treat or prevent the above disease or disorders the dosage forms of the invention may be administered or applied singly, or in combination with other agents. The dosage forms of the invention may also deliver a GABA analog prodrug in combination with another pharmaceutically active agent, including another GABA analog prodrug.

The current invention provides methods of treatment and prophylaxis by administration to a patient a GABA analog prodrug dosage form of the present invention. The patient may be an animal, is more preferably a mammal, and most preferably a human.

The dosage forms of the invention, upon releasing the GABA analog prodrug, preferably provide GABA analogs (e.g., gabapentin and pregablin) upon in vivo administration to a patient. While not wishing to bound by theory, the promoiety or promoieties of the prodrug may be cleaved either chemically and/or enzymatically. One or more enzymes present in the stomach, intestinal lumen, intestinal tissue, blood, liver, brain or any other suitable tissue of a mammal may enzymatically cleave the promoiety or promoieties of the prodrug. The mechanism of cleavage is not important to the current invention. Preferably, GABA analogs formed by cleavage of prodrugs from the compounds used in the invention do not contain substantial quantities of lactam contaminant (preferably, less than 0.5% by weight, more preferably, less than 0.2% by weight, most preferably less than 0.1% by weight) (See Augart et al., U.S. Pat. No. 6,054,482). The extent of release of lactam contaminant from the prodrugs of this invention may be assessed using the standard in vitro analytical methods.

While not wishing to bound by theory, the promoiety or promoieties may be cleaved prior to absorption by the gastrointestinal tract (e.g., within the stomach or intestinal lumen) and/or after absorption by the gastrointestinal tract (e.g., in intestinal tissue, blood, liver or other suitable tissue of a mammal). If the promoiety or promoieties are cleaved prior to absorption by the gastrointestinal tract, the resulting GABA analogs may be absorbed into the systemic circulation conventionally (e.g. via the large neutral amino acid transporter located in the small intestine. If the promoiety or promoieties are cleaved after absorption by the gastrointestinal tract, these GABA analog prodrugs may have the opportunity to be absorbed into the systemic circulation either by passive diffusion, active transport or by both passive and active processes.

If the promoiety or promoieties are cleaved after absorption by the gastrointestinal tract, these GABA analog prodrugs may have the opportunity to be absorbed into the systemic circulation from the large intestine. It is preferred that the promoiety or promoieties are cleaved after absorption by the gastrointestinal tract.

Compositions Useful in the Invention

The present compositions contain a therapeutically effective amount of one or more GABA analog prodrugs, preferably in purified form, together with a suitable amount of a pharmaceutically acceptable vehicle, as to provide the form for proper administration to a patient. When administered to a patient, the prodrug and pharmaceutically acceptable vehicles are preferably sterile. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents. In addition, auxiliary, stabilizing, thickening, lubricating and coloring agents may be used.

In one embodiment, the compositions used in the invention are free of lactam side products formed by intramolecular cyclization. In a preferred embodiment, the compositions used in the invention are stable to extended storage (preferably, greater than one year) without substantial lactam formation (preferably, less than 0.5% lactam by weight, more preferably, less than 0.2% lactam by weight, most preferably, less than 0.1% lactam by weight).

Methods of Use and Doses

The extended release oral dosage forms of GABA analog prodrugs are administered to treat or prevent diseases or disorders such as epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders and/or ethanol withdrawal syndrome.

The amount of GABA analog prodrug that will be effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of a prodrug administered will, of course, be dependent on, among other factors, the subject being treated, the weight of the subject, the severity of the affliction, the manner of administration and the judgment of the prescribing physician.

Preferably, the dosage forms of the invention are adapted to be administered to a patient no more than twice per day, more preferably, only once per day. Dosing may be provided alone or in combination with other drugs and may continue as long as required for effective treatment of the disease state or disorder.

Suitable dosage ranges for oral administration are dependent on the potency of the particular GABA analog drug (once cleaved from the promoiety), but are generally about 0.001 mg to about 200 mg of drug per kilogram body weight. When the GABA analog is gabapentin, typical daily doses of the drug in adult patients are 900 mg/day to 3600 mg/day and the dose of gabapentin prodrug may be adjusted to provide an equivalent molar quantity of gabapentin. Other GABA analogs may be more potent than gabapentin (e.g., pregabalin), and lower doses may be appropriate for both the cleaved drug and any prodrug (measured on an equivalent molar basis). Dosage ranges may be readily determined by methods known to the skilled artisan.

The prodrugs used in the invention are preferably assayed in vitro and in vivo, for the desired therapeutic or prophylactic activity, prior to use in humans. For example, in vitro assays can be used to determine whether administration of a specific prodrug or a combination of prodrugs is preferred for reducing convulsion. The prodrugs may also be demonstrated to be effective and safe using animal model systems.

It will be apparent to those skilled in the art that many modifications, both to materials and methods, may be practiced without departing from the scope of the invention.

Finally, it should be noted that there are alternative ways of implementing both the present invention. Accordingly, the present embodiments are to be considered as illustrative and not restrictive, and the invention is not to be limited to the details given herein, but may be modified within the scope and equivalents of the appended claims.

All publications and patents cited herein are incorporated by reference in their entirety.

What is claimed is:

1. A method of reducing toxicity of an orally administered therapeutic GABA analog, comprising:
   formulating the GABA analog as a prodrug comprised of the therapeutic GABA analog covalently bound to a cleavable promoiety;
   placing the prodrug in a sustained release oral dosage form;
   introducing the dosage form into the intestinal lumen of a patient by having the patient swallow the dosage form;
   releasing the prodrug gradually into the intestinal lumen of the patient over a period of hours; and
   cleaving the promoiety from the prodrug to provide a therapeutic concentration of the GABA analog in the plasma of the patient, wherein the dosage form releases from 0 to 20% of the prodrug in 0 to 2 hours, from 20 to 50% of the prodrug in 2 to 12 hours, from 50 to 85% of the prodrug in 3 to 20 hours and greater than 75% of the prodrug in 5 to 18 hours.

2. The method of claim 1, wherein the toxicity of the GABA analog administered from said sustained release oral dosage form is less than the toxicity of an equivalent dose of the GABA analog administered from an immediate release oral dosage form.

3. The method of claim 1, wherein the toxicity of the promoiety administered from said sustained oral release dosage form, and any metabolites thereof, is less than the toxicity of the promoiety, and any metabolites thereof, administered at an equivalent dose from an immediate release oral dosage form.

4. The method of any of claims 1 to 3, wherein the promoiety metabolizes to form an aldehyde.

5. The method of claim 4, wherein the aldehyde comprises formaldehyde.

6. The method of any one of claims 1 to 3, wherein the promoiety metabolizes to form an acid that depletes carnitine in said patient.

7. The method of claim 6, wherein the acid comprises pivalic acid.

8. The method of claim 1, wherein the period of hours comprises at least about 6 hours.

9. The method of claim 1, wherein the period of hours comprises at least about 8 hours.

10. The method of claim 1, wherein the period of hours comprises at least about 12 hours.

11. The method of claim 1, wherein the concentration of the GABA analog in plasma of the patient over time provides a curve of concentration of the GABA analog in the plasma over time, the curve having an area under the curve (AUC) which is proportional to the dose of GABA analog administered.

12. The method of claim 11, wherein the curve has a maximum plasma concentration ($C_{max}$) which is proportional to the dose of GABA analog administered.

13. The method of any one of claims 1, 11 or 12, wherein the $C_{max}$ is less than 75% of the $C_{max}$ obtained from administering an equivalent dose of the prodrug from an immediate release oral dosage form, and the AUC is at least 50% of the AUC obtained from administering an equivalent dose of the prodrug from an immediate release oral dosage form.

14. The method of any one of claims 1, 11 or 12, wherein the $C_{max}$ is less than 60% of the $C_{max}$ obtained from administering an equivalent dose of the prodrug from an immediate release oral dosage form, and the AUC is at least 75% of the AUC obtained from administering an equivalent dose of the prodrug from an immediate release oral dosage form.

15. The method of claim 13, wherein the AUC is substantially the same as the AUC obtained from administering an equivalent dose of the prodrug from an immediate release oral dosage form.

16. The method of claim 14, wherein the AUC is substantially the same as the AUC obtained from administering an equivalent dose of the prodrug from an immediate release oral dosage form.

17. A method of orally administering a GABA analog prodrug, comprising:
   formulating the GABA analog as a prodrug comprised of the therapeutic GABA analog covalently bound to a cleavable promoiety;
   placing the prodrug in a sustained release oral dosage form;
   introducing the dosage form into the intestinal lumen of a patient by having the patient swallow the dosage form;
   releasing the prodrug gradually from the swallowed dosage form into the intestinal lumen of the patient over a period of hours; and
   allowing the GABA analog to be cleaved from the promoiety after said swallowing to provide a therapeutic concentration of the GABA analog in the plasma of the patient wherein the dosage form releases from 0 to 20% of the prodrug in 0 to 2 hours, from 20 to 50% of the prodrug in 2 to 12 hours, from 50 to 85% of the prodrug in 3 to 20 hours and greater than 75% of the prodrug in 5 to 18 hours.

18. The method of claim 17, wherein the promoiety metabolizes to form an aldehyde.

19. The method of claim 18, wherein the aldehyde comprises formaldehyde.

20. The method of claim 17, wherein the promoiety metabolizes to form an acid that depletes carnitine in said patient.

21. The method of claim 17, wherein the period of hours comprises at least about 6 hours.

22. The method of claim 17, wherein the period of hours comprises at least about 8 hours.

23. The method of claim 17, wherein the period of hours comprises at least about 12 hours.

24. The method of claim 17, wherein the concentration of the GABA analog in plasma of the patient over time provides a curve of concentration of the GABA analog in the plasma over time, the curve having an area under the curve (AUC) which is proportional to the dose of GABA analog administered.

25. The method of claim 17, wherein the curve has a maximum plasma concentration ($C_{max}$) which is proportional to the dose of GABA analog administered.

26. The method of claim 24 or 25, wherein the $C_{max}$ is less than 75% of the $C_{max}$ obtained from administering an equivalent dose of the prodrug from an immediate release oral dosage form and the AUC is at least 50% of an AUC obtained from administering an equivalent dose of the prodrug from an immediate release oral dosage form.

27. The method of claim 24 or 25, wherein the $C_{max}$ is less than 60% of the $C_{max}$ obtained from administering an equivalent dose of the prodrug from an immediate release oral dosage form and the AUC is at least 75% of an AUC obtained from administering an equivalent dose of the prodrug from an immediate release oral dosage form.

28. The method of claim 26, wherein the AUC is substantially the same as the AUC obtained from administering an equivalent dose of the prodrug from an immediate release oral dosage form.

29. The method of claim 27, wherein the AUC is substantially the same as the AUC obtained from administering an equivalent dose of the prodrug from an immediate release oral dosage form.

* * * * *